US008574495B2

(12) United States Patent
Pellicer Sancho

(10) Patent No.: US 8,574,495 B2
(45) Date of Patent: Nov. 5, 2013

(54) APPARATUS FOR AUTOMATIC ANALYSIS OF SAMPLES ON GEL CARDS

(75) Inventor: Marc Pellicer Sancho, Barcelona (ES)

(73) Assignee: Grifols, S.A., Barcelona (ES)

( * ) Notice: Subject to any disclaimer, the term of this patent is extended or adjusted under 35 U.S.C. 154(b) by 701 days.

(21) Appl. No.: 12/469,355

(22) Filed: May 20, 2009

(65) Prior Publication Data

US 2009/0293644 A1  Dec. 3, 2009

(30) Foreign Application Priority Data

May 30, 2008  (ES) .................................. 200801622

(51) Int. Cl.
G01N 21/00  (2006.01)

(52) U.S. Cl.
USPC .................. 422/65; 422/63; 422/64; 422/66; 422/67; 422/536; 436/180

(58) Field of Classification Search
USPC ............... 422/63–67, 536; 436/180
See application file for complete search history.

(56) References Cited

U.S. PATENT DOCUMENTS

| 5,681,530 | A | | 10/1997 | Kuster et al. |
| 6,162,399 | A | * | 12/2000 | Martinell Gisper-Sauch . 422/64 |
| 2003/0215357 | A1 | * | 11/2003 | Malterer et al. ................. 422/50 |
| 2007/0202011 | A1 | | 8/2007 | Nogawa et al. |
| 2008/0063567 | A1 | | 3/2008 | Schacher et al. |

FOREIGN PATENT DOCUMENTS

| EP | 0 965 842 A1 | 12/1999 |
| EP | 0 628 822 B1 | 2/2002 |
| EP | 0 918 221 B1 | 9/2006 |
| JP | 61-038648 A | 2/1986 |
| JP | 02-119958 A | 5/1990 |
| JP | 06-074958 A | 3/1994 |
| JP | 11-108937 A | 4/1999 |
| JP | 2002-243746 A | 8/2002 |
| JP | 2003-083994 A | 3/2003 |
| JP | 2005-077312 A | 3/2005 |
| JP | 2007-527525 A | 9/2007 |
| WO | WO 95/08774 A2 | 3/1995 |
| WO | WO 97/44671 A1 | 11/1997 |
| WO | WO 2005/044453 | 5/2005 |

OTHER PUBLICATIONS

Office Actions dated Feb. 14, 2011 and Aug. 29, 2011, issued in the corresponding Chile Patent Application No. 1318-2009.
An English Translation of the Office Action (Notice of Reasons for Rejection) dated Oct. 25, 2011, issued in the corresponding Japanese Patent Application No. 2009-130955.
Search Report dated Dec. 1, 2011, issued in the corresponding Spanish Patent Application No. 200801622.

* cited by examiner

*Primary Examiner* — Jyoti Nagpaul
(74) *Attorney, Agent, or Firm* — RatnerPrestia

(57) ABSTRACT

The apparatus comprises a single transportable structure provided with several separate compartments located in a vertical stack within a cabinet, with means for the vertical transport of gel cards, means for the transport of units for moving the cards and pipetting probes, being displaceable to the entire transverse cross-section of the compartments in at least two of the vertical compartments or floors through moving along coordinate axes X, Y, Z at right-angles, and control means so that automatic functioning can take place simultaneously with manual actions to load and unload the necessary materials (samples, reagents, cards, wash solutions and waste solutions) in a random manner.

20 Claims, 38 Drawing Sheets

APPARATUS FOR AUTOMATIC ANALYSIS OF SAMPLES ON GEL CARDS

This invention discloses new equipment which can be used for the automatic analysis of blood samples on gel cards.

The equipment is aimed to allow analyses to be performed completely, that is, from insertion of the samples into the apparatus to acquisition of the results of the analyses.

The apparatus to which the invention relates is characterised in that it has means for continuous operation, but which also allows for the manual insertion of samples, reagents and/or cards or the provision or removal of containers for waste liquid, wash solutions and waste cards or any other type of work on the equipment simultaneously with normal automatic operation of the apparatus, thus achieving high productivity in that different types of analyses can be performed at the same time as the manual handling required for the specific apparatus.

Access to reagents, samples, cards, waste cards and waste liquids can take place randomly.

One characteristic of the apparatus to which this invention relates comprises its construction in the form of a vertical column with various floors of devices which together perform all the functions of the apparatus, providing a very compact arrangement of the same, taking up minimum space in its horizontal projection. This arrangement provides appreciable advantages from the point of view of the use of space in laboratories or clinical centres and also appreciable ergonomics in the relationship between the apparatus and the personnel using it, who can carry out all the functions necessary for it from a single position with respect to the apparatus.

A number of forms of apparatus for the automatic acquisition of the results of the analysis of samples on gel cards are currently known, such as PE 0628822 by Orto Diagnostics Systems Inc., and also PE 00402773 by the Applicant. Nevertheless, these known pieces of apparatus cannot be used continuously and randomly like the equipment to which this invention relates, and also their structure is of the polar type, based on sets of supports for the samples and reagents which rotate around a central axis.

In the apparatus to which this invention relates the gel cards are moved either on their own floor by a transport system which covers the entire surface area of the floor along the X, Y, Z coordinate axes or by means of devices for ascending and descending between the upper floor on which the reagents, samples and gel cards are pipetted, and the intermediate floor of the apparatus bearing the cards and the reagents, and vice versa. The devices for ascending and descending between floors are card carriers to receive the prepared samples and also to support the cards of samples for the required time during incubation periods. Obviously they also have the ability to move vertically on each floor.

The lower floor holds the containers for wash solutions, waste liquids and waste used cards, as well as the fluidic system which is fundamentally designed to control external and internal washing of the pipetting probes and the wells in which dilutions are performed.

The apparatus has incorporated control means comprising a computer and a touch screen enabling both automated control of the apparatus in accordance with the software used and display of the results or other operating data for the apparatus.

The wash system essentially comprises two tanks located on the lower floor intended for each of the two wash and rinse solutions respectively, as well as a system of pumps for pumping the wash liquids and for sucking out the same after the stage of washing the pipetting probes and the stirrer dilution devices.

The gel cards are centrifuged in suspended centrifuges to permit simpler handling for maintenance and cleaning, to permit dismantling from the bottom through simple dismantling of the suspended centrifuge, the cards being fed through the windows in the top covers of the centrifuges.

Another advantageous feature of the apparatus according to this invention arises from the multiple nature of many of its components to permit continuous operation with a large capacity for analysis, permitting random access for reagents, samples, cards, waste cards and waste liquids.

In order to provide a better understanding drawings of a preferred embodiment are appended by way of an example of the apparatus according to this invention which will provide a basis for the detailed description thereof without restricting the scope of this invention.

Figure 29:
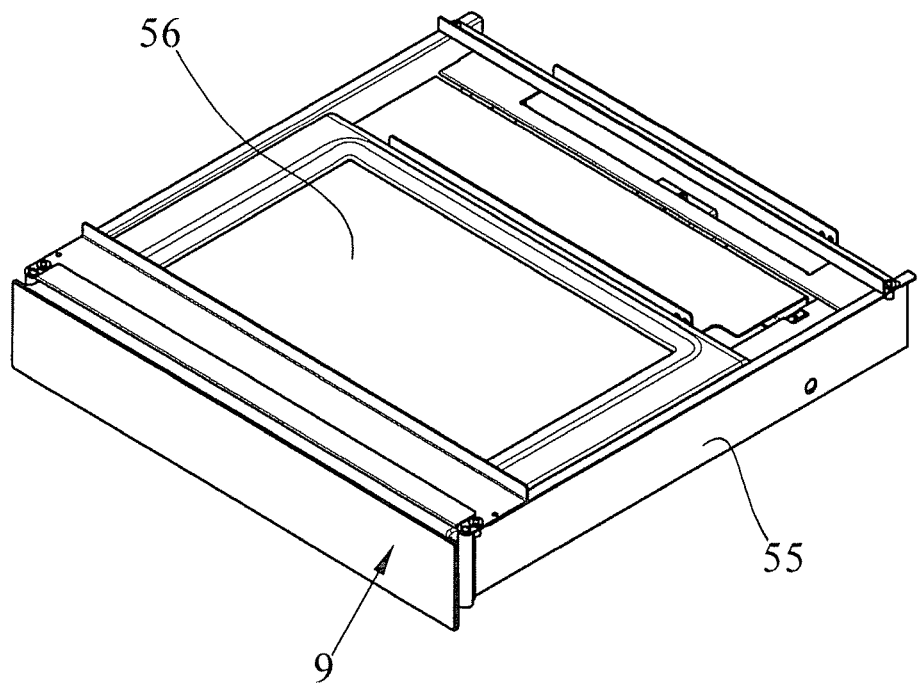
Figure 30:
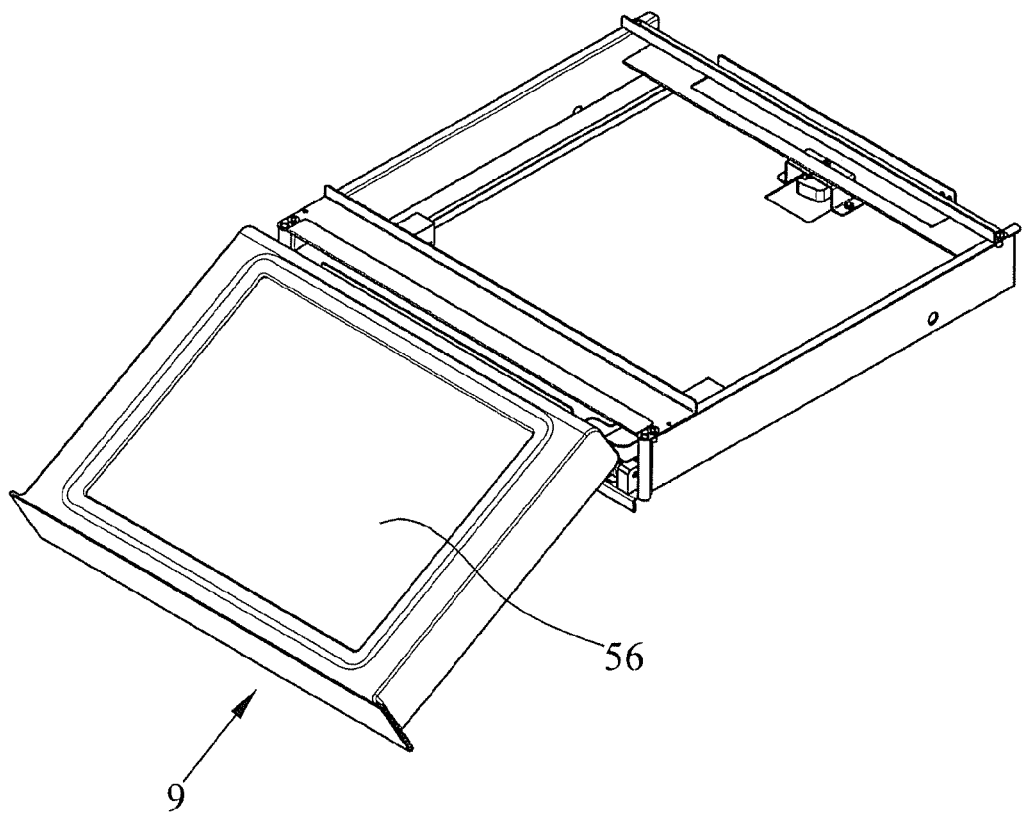

FIGS. 29 and 30 both show perspective views of the touch screen in the closed position and in the opened out position.

Figure 31:
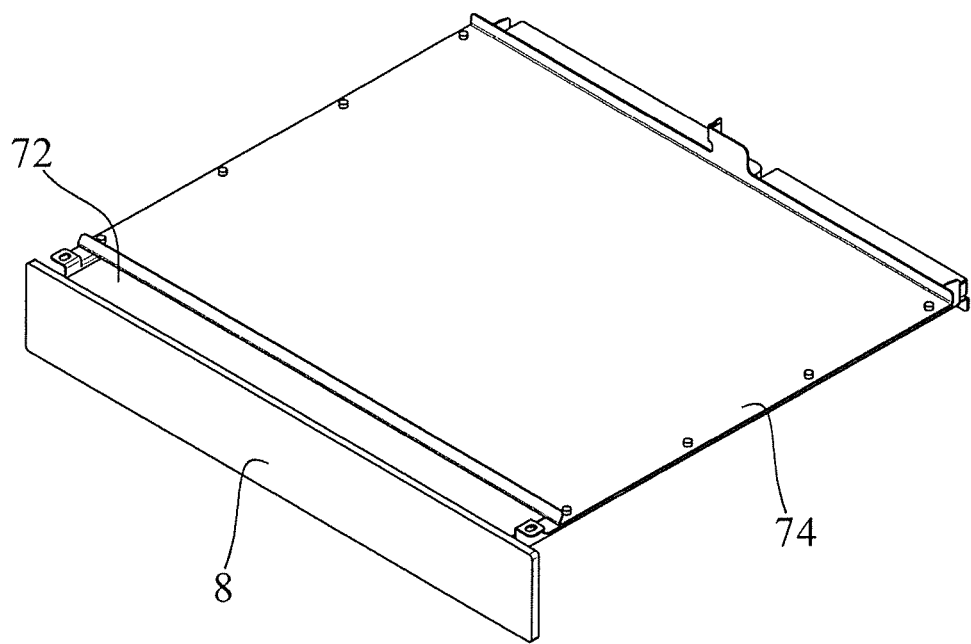
Figure 32:
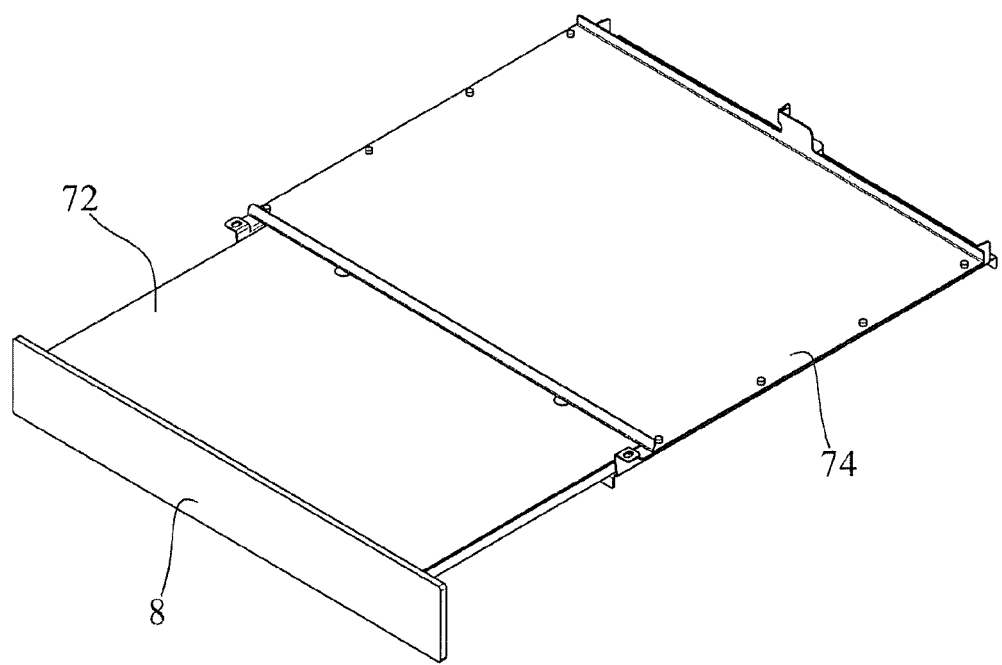

FIG. 31 and 32 each show views of the work surface which can be accessed from the front of the apparatus in the storage and use positions respectively.

Figure 33:
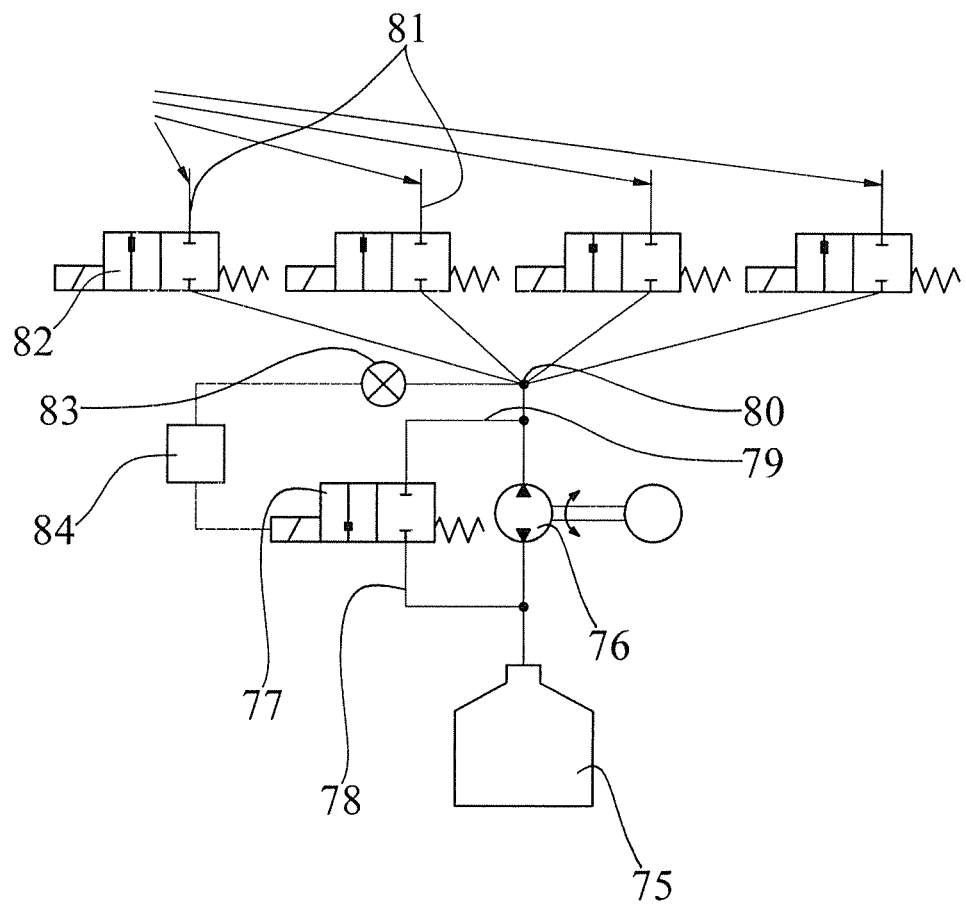

FIG. 33 shows a diagrammatical drawing of the fluidic device controlling the pressure of the apparatus.

Figure 34:
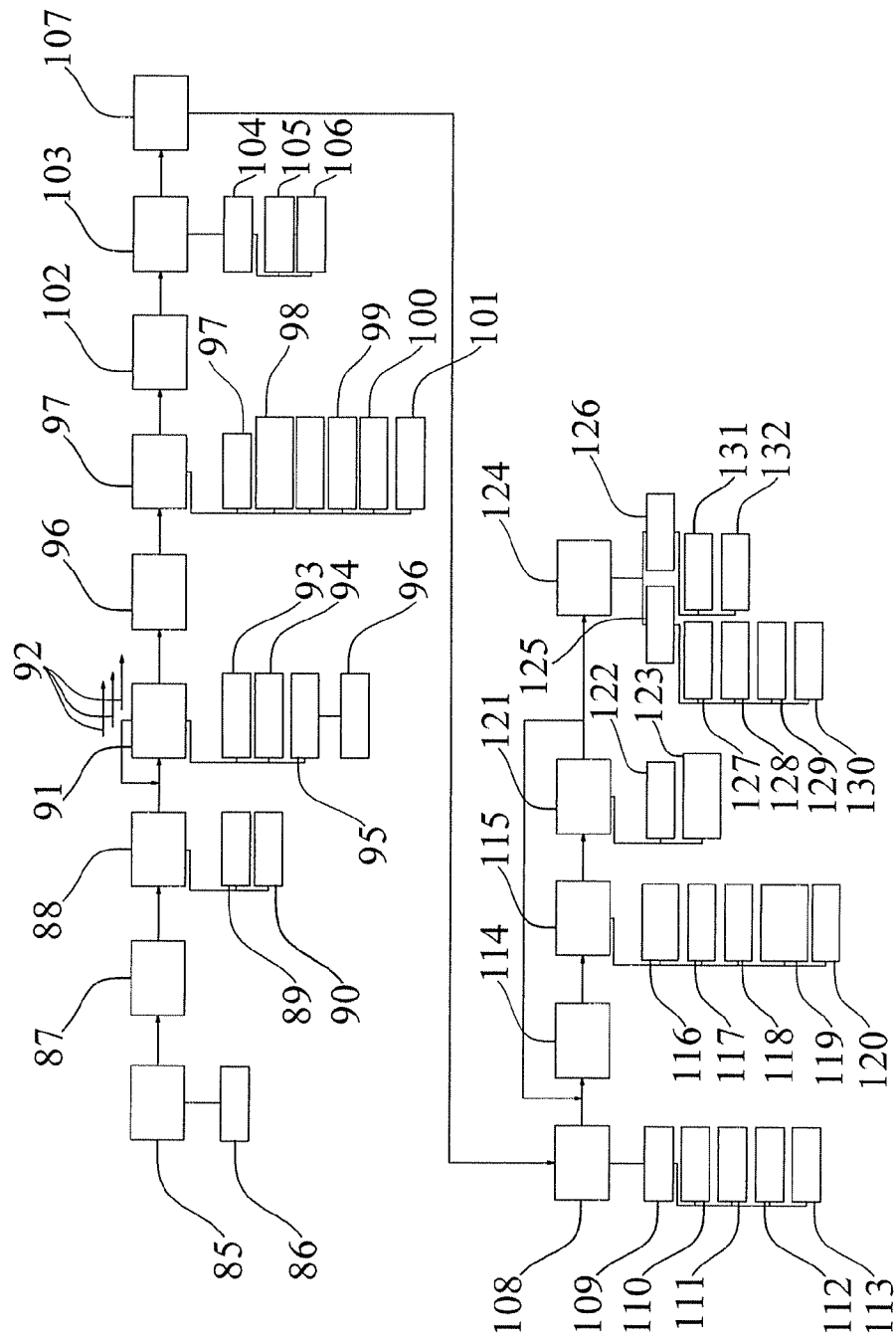
Figure 35:
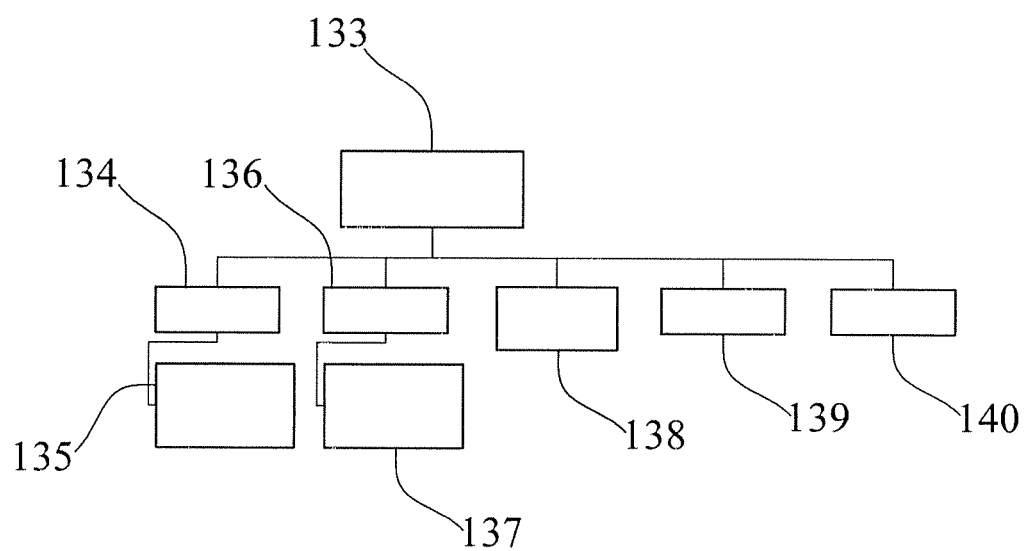

FIGS. 34 and 35 both show illustrations of flow diagrams of the functioning of the apparatus.

Figure 36:
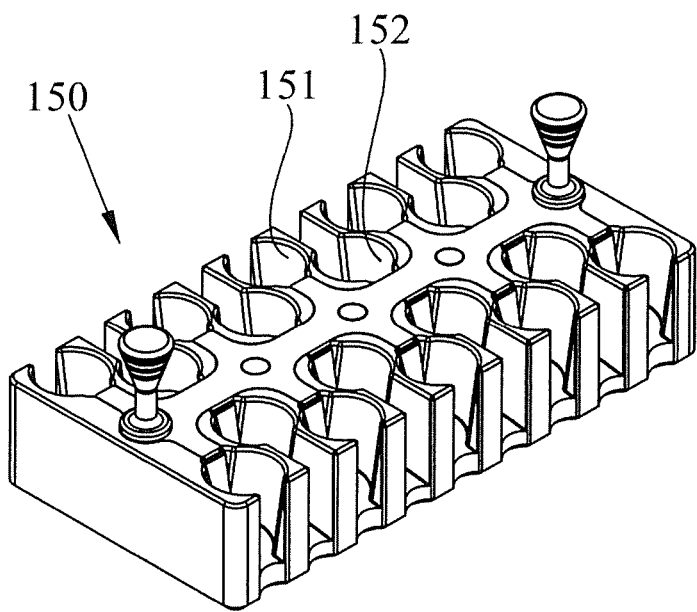

FIG. 36 shows a perspective view of the reagents stand.

Figure 37:
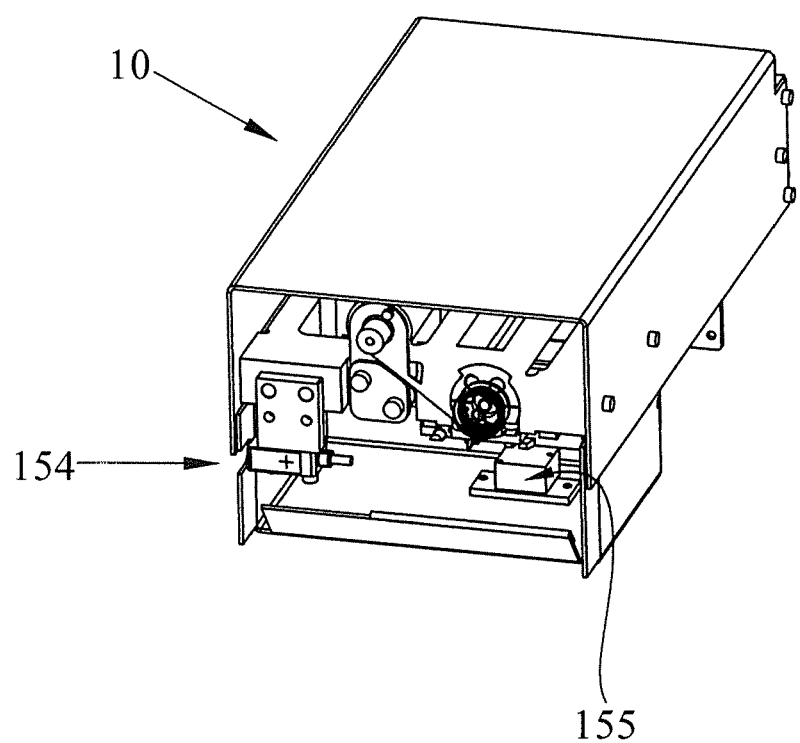

FIG. 37 shows a perspective view of the clamp holder showing the laser and bar detectors.

Figure 38:
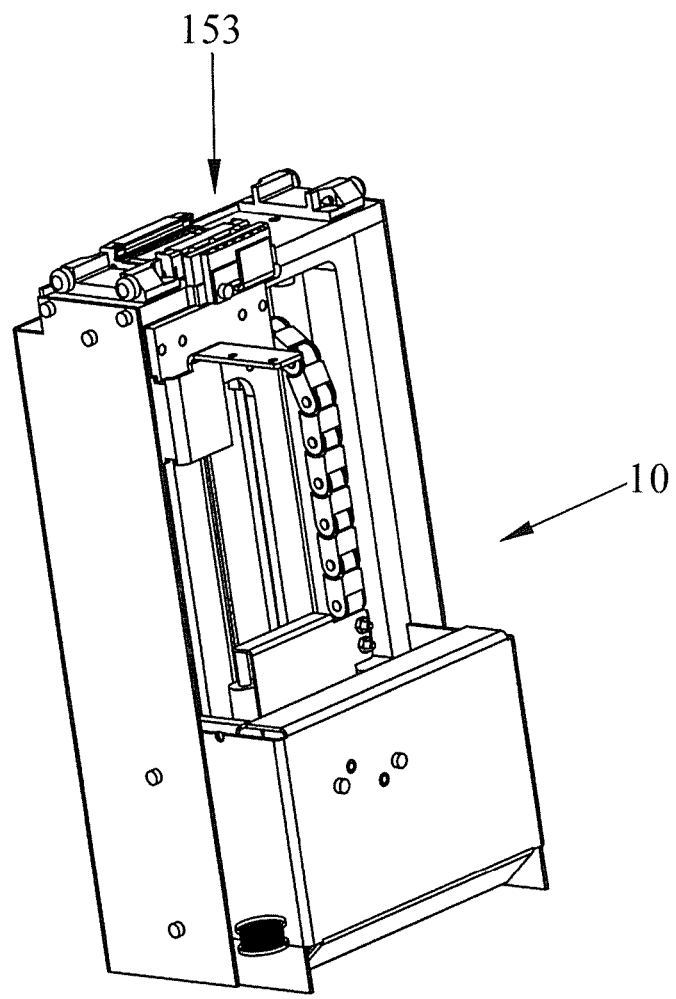

FIG. 38 shows a view of the unit in FIG. 37 illustrating the clamp.

Figure 1:
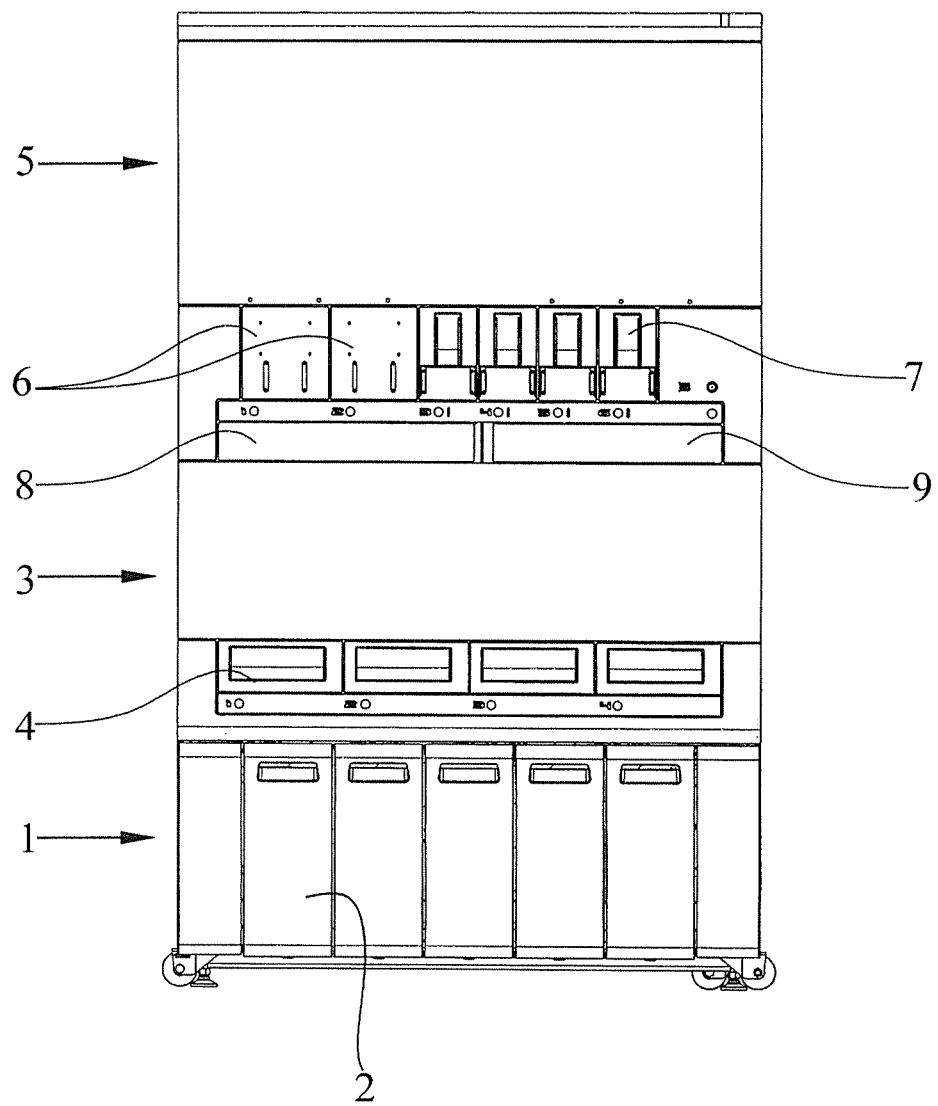
FIG. 1 shows a view of the apparatus according to this invention in front elevation, in the operating position.
Figure 2:
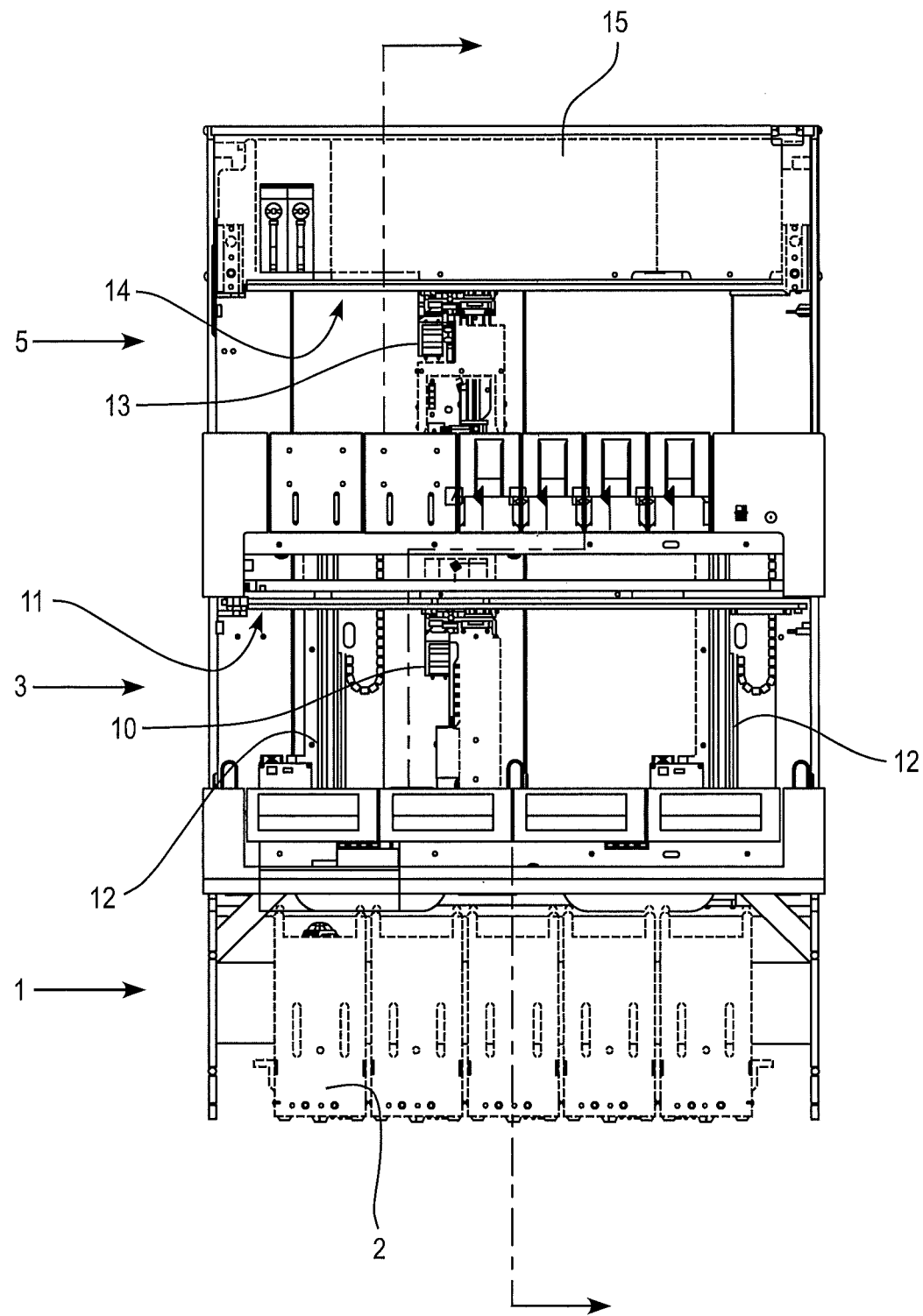
FIG. 2 shows a front view of the apparatus with some of the front covers and components removed so that the layout of some of the components within can be appreciated.
Figure 3:
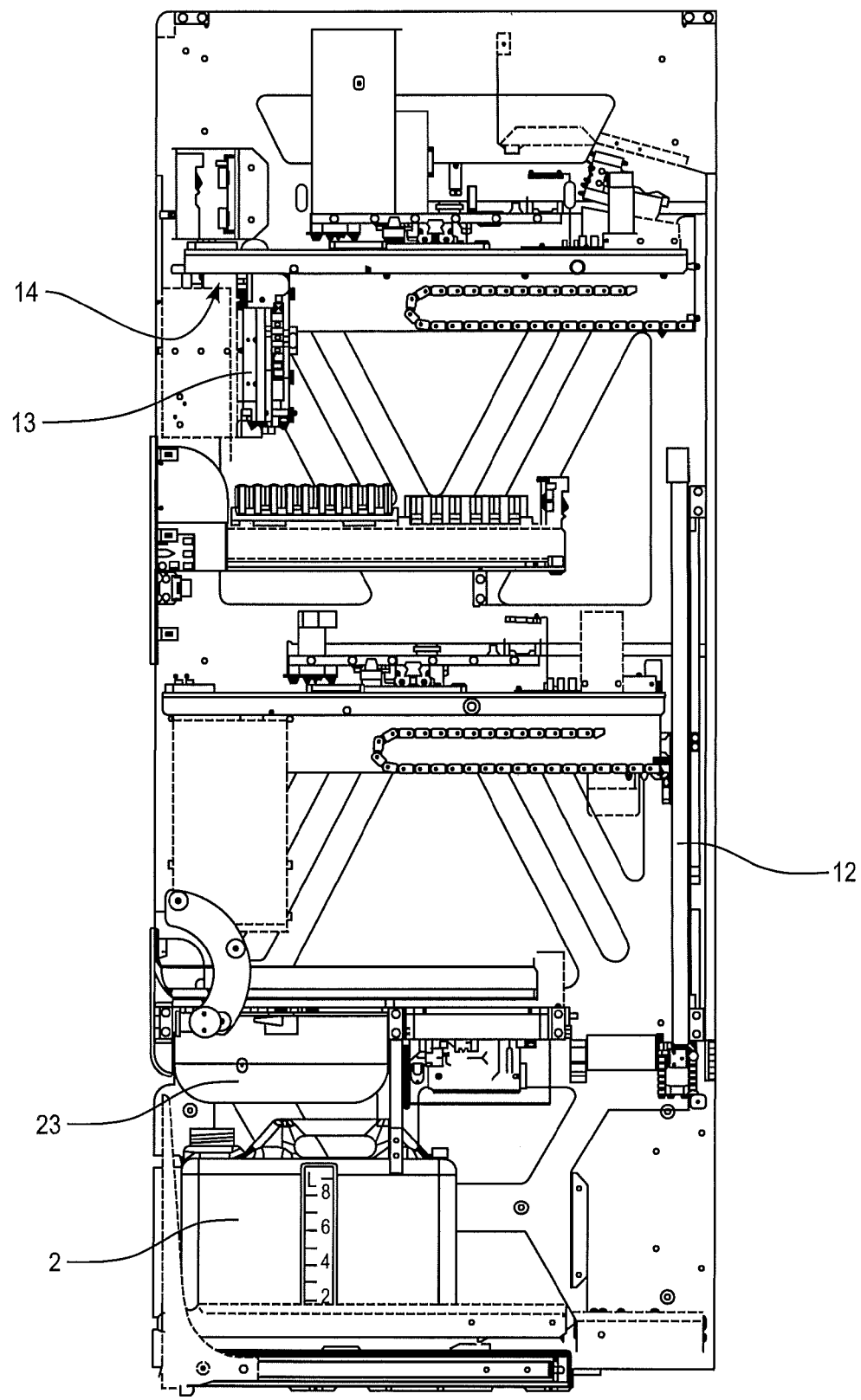
FIG. 3 shows a side view of the apparatus showing the general layout of the components within it.

The general construction of the apparatus corresponds to a distribution on various superimposed floors in a single cabinet, as will be seen in FIGS. 1, 2 and 3. The single cabinet has a front surface on which the various controls and handling devices are located, FIG. 1 showing a lower floor -1- for the containers for the different liquids and for collecting wastes, comprising a series of boxes -2- of variable number which can be accessed from the front, the first two being intended to hold bottles for wash solutions, followed by a container for waste cards and finally two boxes for waste liquids. On said floor -1- there is also the electronic unit for control of the fluidic system for the equipment. On intermediate floor -3- the apparatus includes a number of boxes for the insertion of cards on their original supports, these being indicated by the number -4-, as well as centrifuges for 12 cards each, incubators and a reader, as will be seen in greater detail below. Each of the boxes is supported by right-angled guides which ensure that there is no oscillation when they are open. They are opened by means of an electrical safety lock, for the operation of which the software controlling the apparatus must be consulted. It likewise contains an arm for rectilinear movement with a clamp for transporting cards from any of the modules, with X, Y, Z movement capacity. A set of incubators can move vertically to transport the cards between the intermediate floor and the upper floor, as will be explained in greater detail below. Upper floor -5- contains two boxes -6- for the introduction of reagents and four boxes -7- for the insertion of samples, as well as a double well for performing dilutions and an arm moving in a straight line on coordinates for pipetting samples and reagents onto the cards, as will be seen in greater detail below. From the front surface of the apparatus access may also be gained to control and accessory components such as a folding worktop -8- and a screen -9-, which can be likewise withdrawn into the body of the apparatus.

FIG. 2 shows the general construction of the apparatus in greater detail, shown with some of the covers removed. Thus for example various removable containers -2- which are intended to contain the wash solutions and receive waste liquids and waste cards will be seen on the lower floor. It will be noted that the apparatus will be equipped with wheels for moving it, shown in FIG. 1, but not shown in FIGS. 2 and 3 as these are illustrations of the partly dismantled apparatus.

FIG. 2 shows a unit -10- which can move along the system of coordinate axes between upper guides -11- to cover the entire transverse cross-section of the intermediate floor in which it moves with various items for the movement of individual cards which will be explained in greater detail. This view also shows one of the vertical guides -12- for an incubator ascent device. The unit is also provided with a bar code reader for the labels on the cards and a laser sensor to detect the presence of cards in the supports in the boxes.

FIG. 2 likewise shows upper unit -13- which like unit -10- can move according to a system of X and Y coordinate axes on upper guides -14- to cover the entire transverse surface area of the apparatus to permit samples and reagents to be pipetted onto the cards, and for the cards to be read. Various control components of the electronic and fluidic assembly for it are included in upper part -15- of the apparatus. The unit contains two pipetting probes with a spacing identical to the spacing between samples and cards. Two extractions may take place at the same time.

Figure 4:
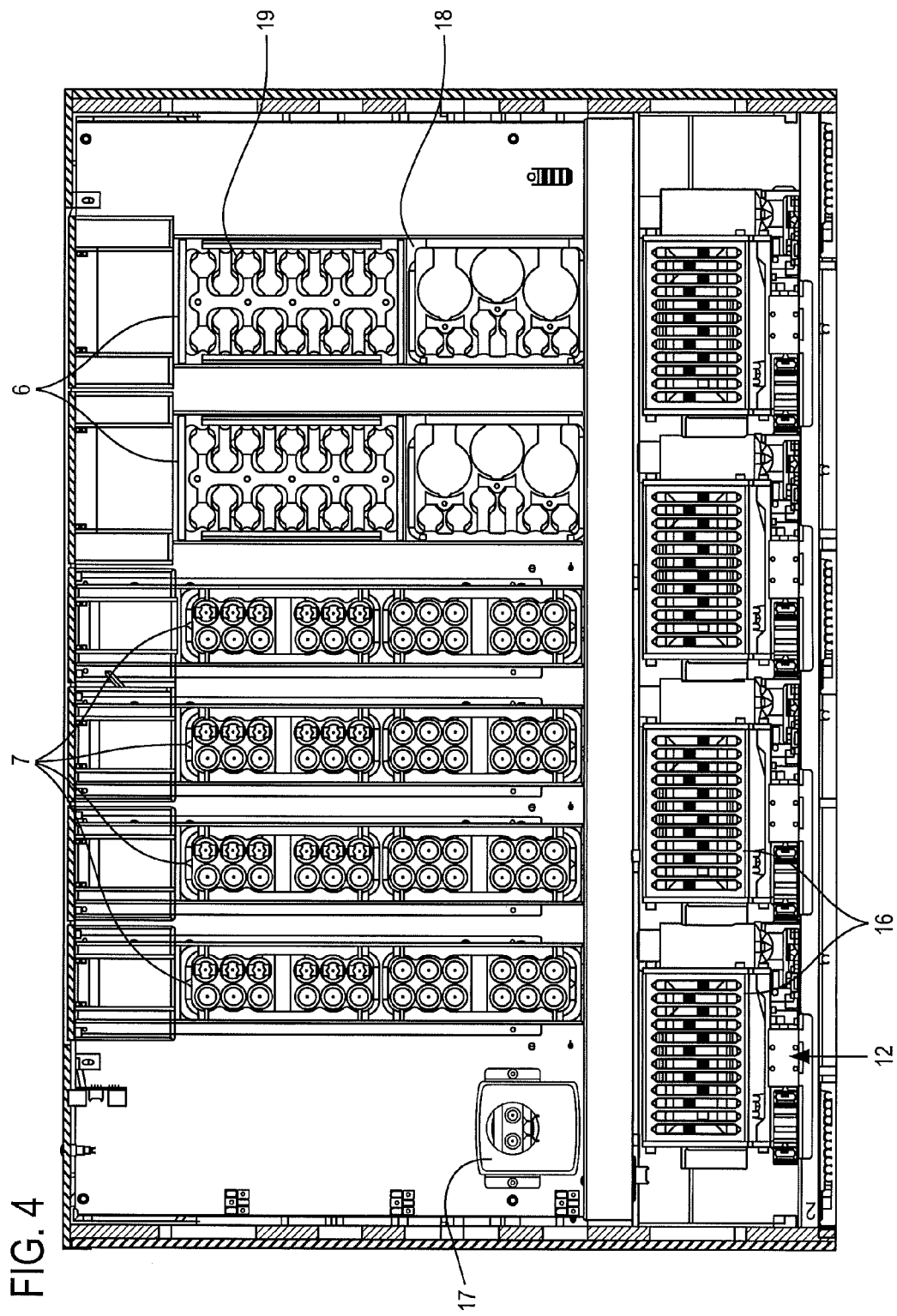
FIG. 4 shows a plan view corresponding to the upper floor, holding samples, reagents and diluents.

FIG. 4 shows a plan view of the upper floor of the apparatus showing the two boxes for reagents and diluents -6- requiring stirring and the four boxes -7- for samples, as well as four sample incubator heaters -16-, each of which is associated with an ascending device with guides -12- previously shown in FIGS. 2 and 3. Within each incubator the cards are supported by opposing magnets which form a magnetic clamp that prevents the cards from moving during pipetting. On the upper floor there is also a double well -17- for performing dilutions, as well as the pipetting unit and arm which cannot be seen in the illustration and plan in FIG. 4. FIG. 4 also shows the separate arrangement of the set of supports for diluents and reagents -18- which do not need to be stirred and a set of receivers -19- for reagents which do need stirring, for which there is an orbital stirring device which will be explained in greater detail below, all within removable front box -6-.

Figure 5:
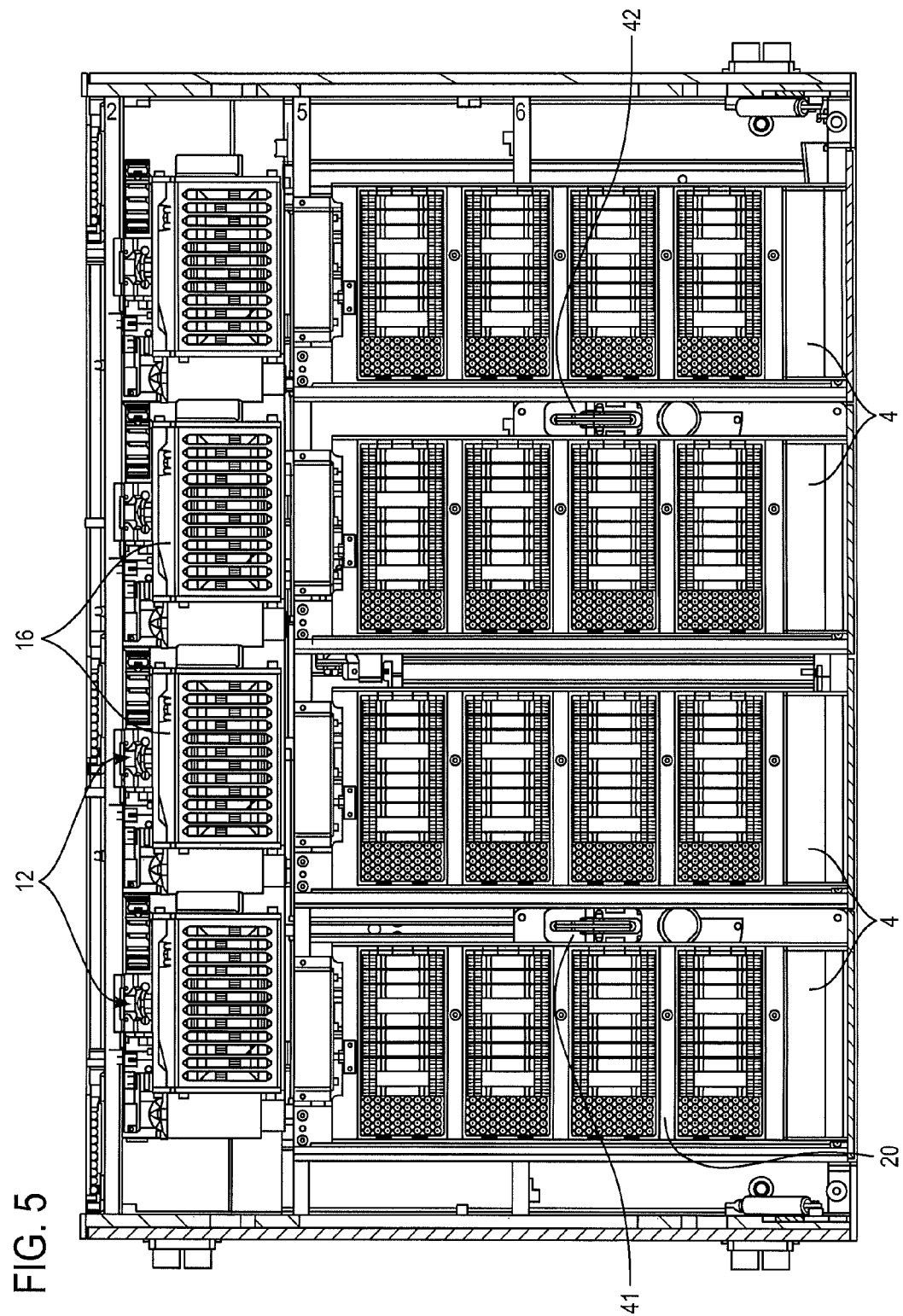
FIG. 5 shows a plan view of the intermediate floor of the apparatus showing the supports for the gel cards and the heating and lifting devices.

FIG. 5 shows incubators -16- and guides -12- for vertical movement, that is to achieve a lifting function between the intermediate floor and the upper floor, and boxes -4- for the cards which are incorporated in "racks" or standard supports -20-.

Figure 6:
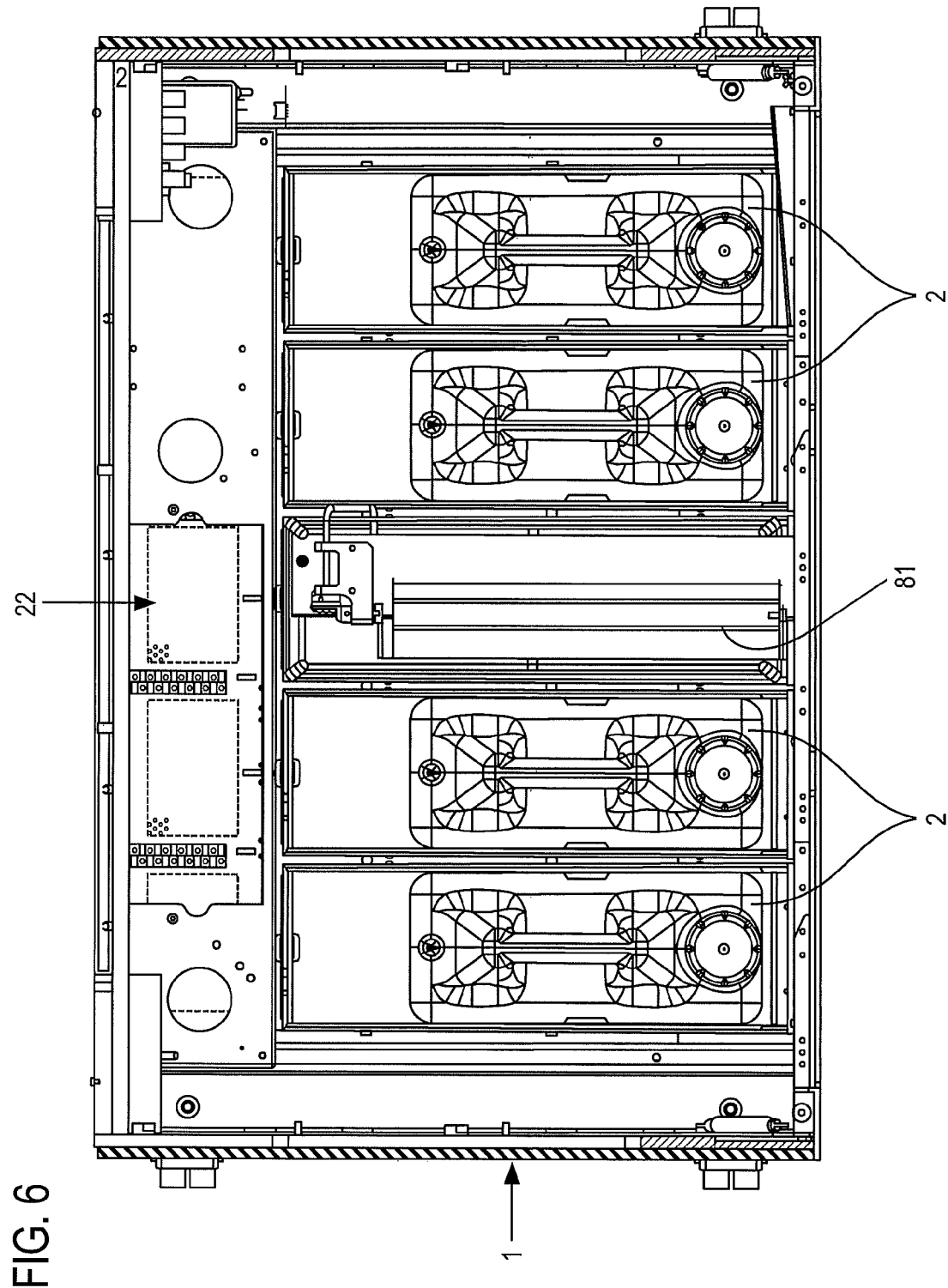
FIG. 6 shows a plan view of the lower floor of the apparatus which is intended to hold liquids for reactions, to receive spent cards and a fluidics assembly to control washing of the pipetting probes.

FIG. 6 shows a plan view of the lower floor on which are stored various boxes with bottles of wash solutions, bottles for waste liquids and a container for waste cards. Although the number of containers or bottles for liquids may vary, in the situation illustrated there is a total of four boxes with containers or bottles -2-, as well as a central box for waste cards, with a central container -21- designed to receive used cards as a buffer function while the box for wastes is removed, that is it can be placed in the operating position or may be caused to rotate manually as will be shown in greater detail below. Rear part -22- of the lower floor is intended to contain the fluidic system for the apparatus as well as its control electronics.

Figure 7:
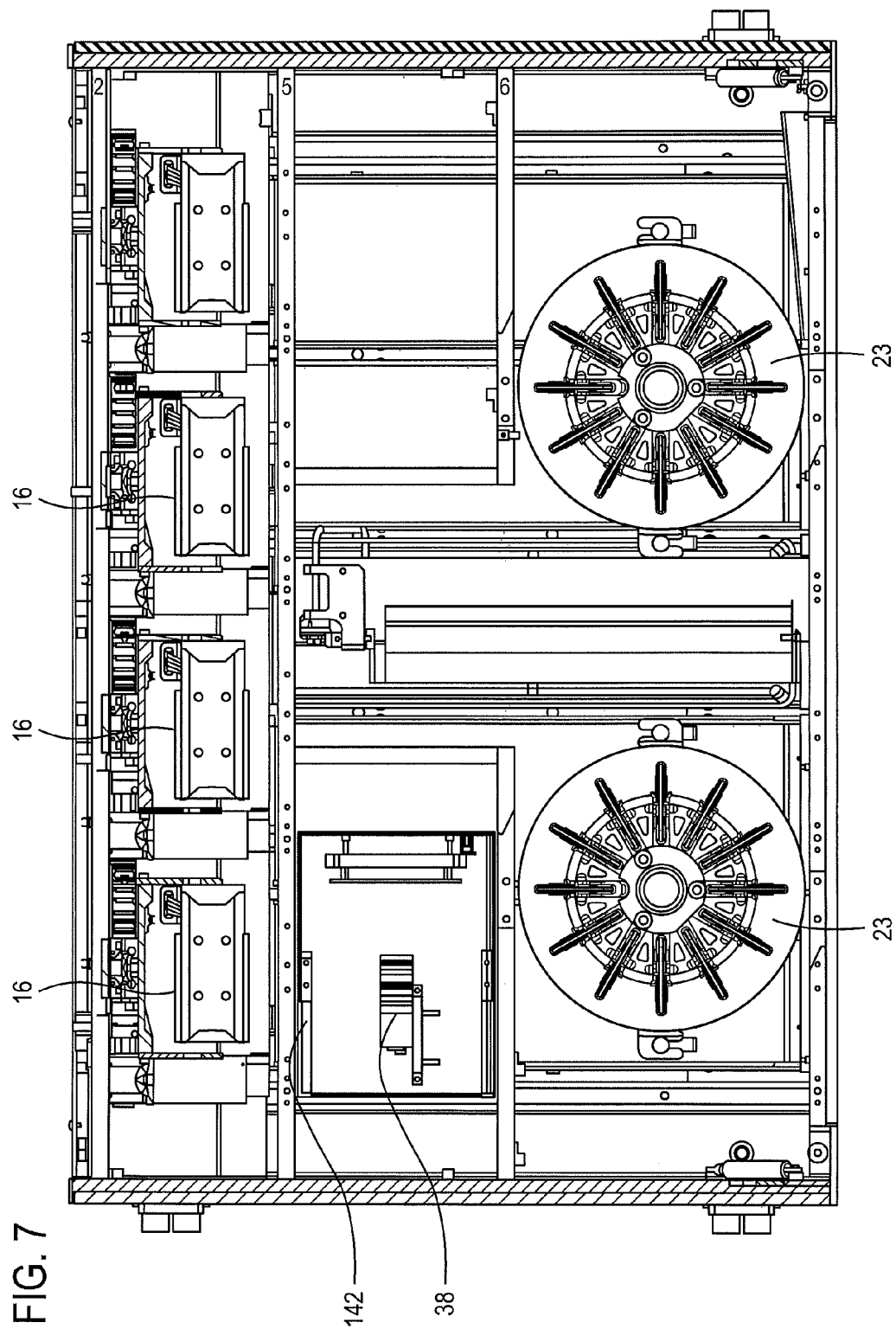
FIG. 7 shows a diagrammatical view of the arrangement of the centrifuges, the reader and the incubator heater devices.

On the base of the intermediate floor, which is shown in a view from below in FIG. 7, there are centrifuges -23-, two in number in the apparatus provided by way of example. Each of the centrifuges has a number of radial grooves, twelve for each centrifuge in the case illustrated, for centrifuging the gel cards. Heaters -16- for the gel cards and card reader body -142-, with reader device -38- can be seen in that view.

Figure 8:
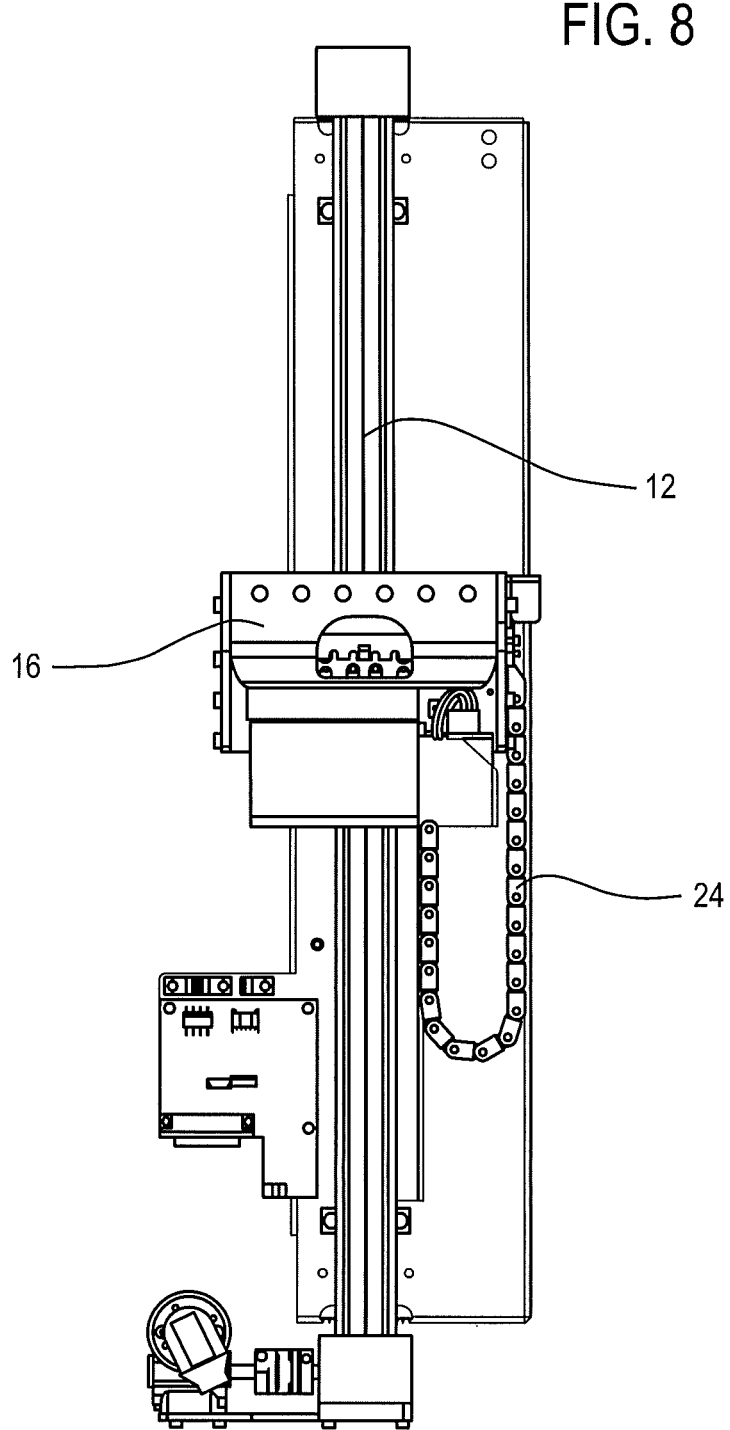
FIG. 8 shows a diagrammatical front view of a heater device and elevator.

FIG. 8 shows a heating and lifting assembly, that is to say an incubator and lift device for the gel cards to be raised between the intermediate floor and the upper floor. Each of the said assemblies comprises a guide -12- and a heater -16- driven and guided along the said guide, being electrically connected by flexible connection -24-.

Figure 9:
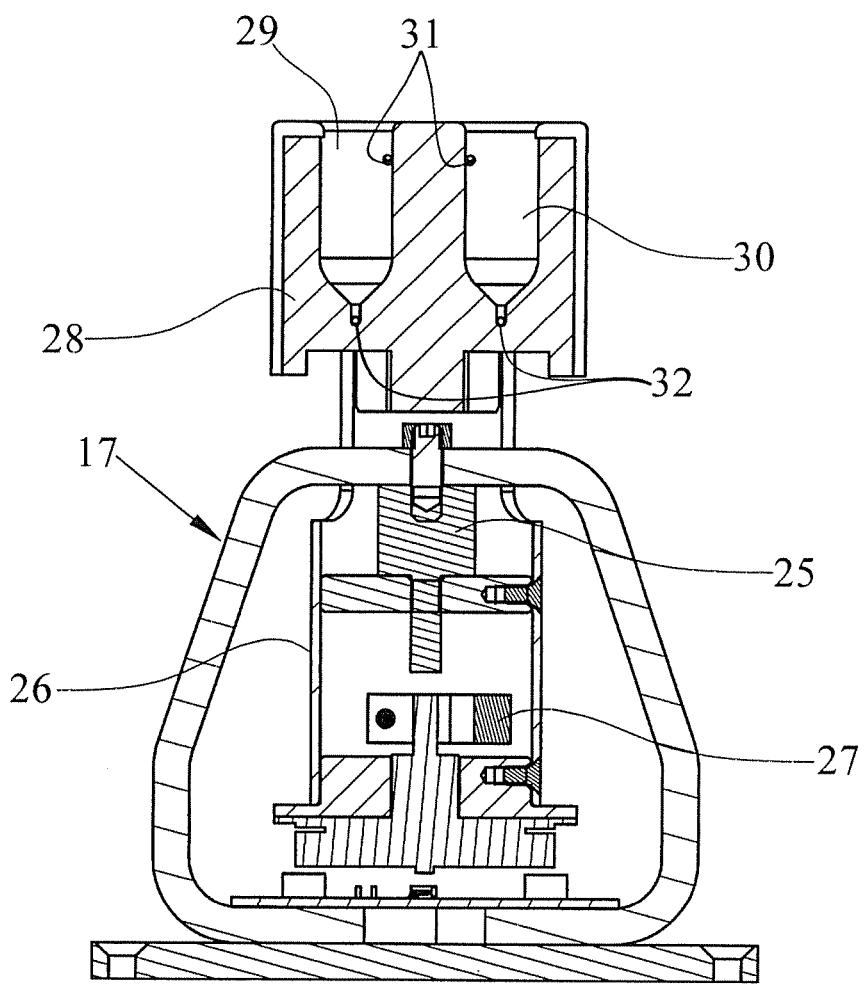
FIGS. 9 and 10 show a view in cross-section and plan respectively of the double self-stirred device or well for dilutions carried out in the apparatus.
Figure 10:
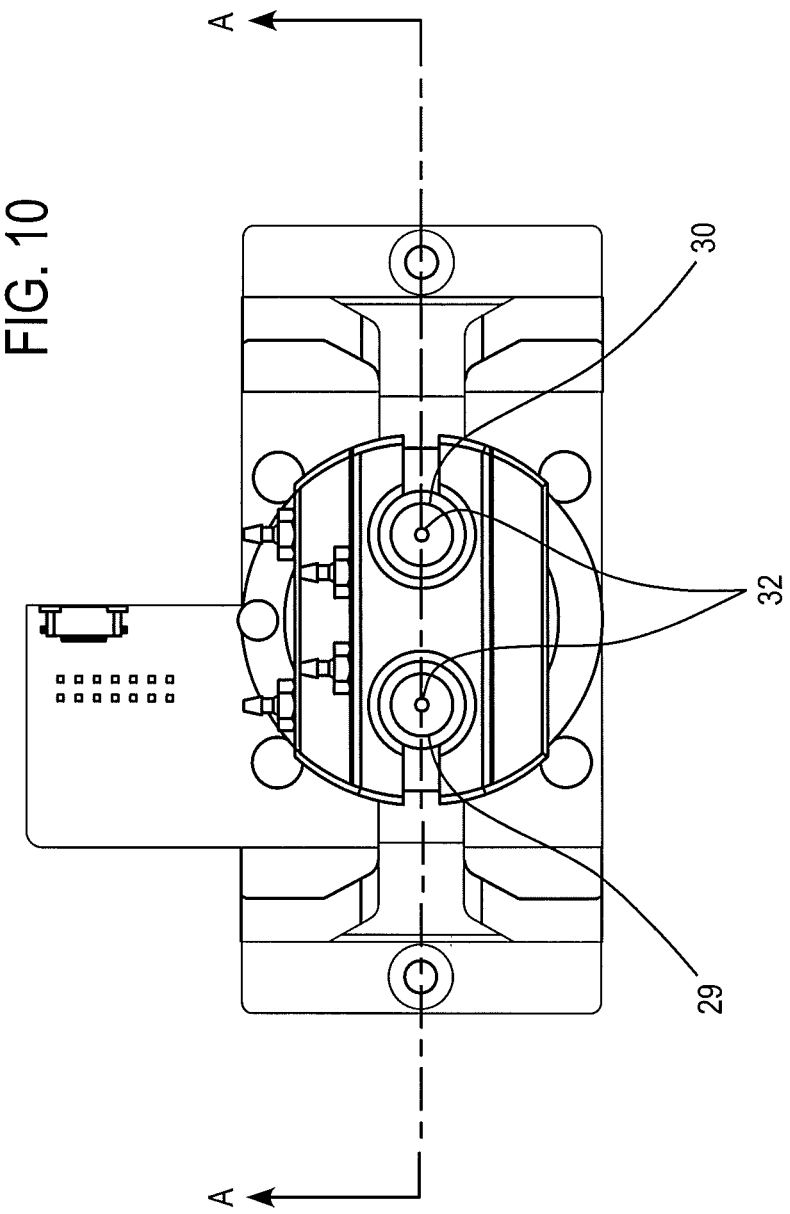

FIGS. 9 and 10 show the double device or "well" for performing dilutions, which comprises a carrier body -17-, with an intermediate resilient block or "silent block" -25-, body -26- which carries the eccentric mass -27- producing orbital stirring in the set of double wells -28-. This double well -28- has cavities -29- and -30- provided with inlets -31- and outlets -32- for liquids at the bottom. Body -17- is attached to a lower fixed base.

Figure 11:
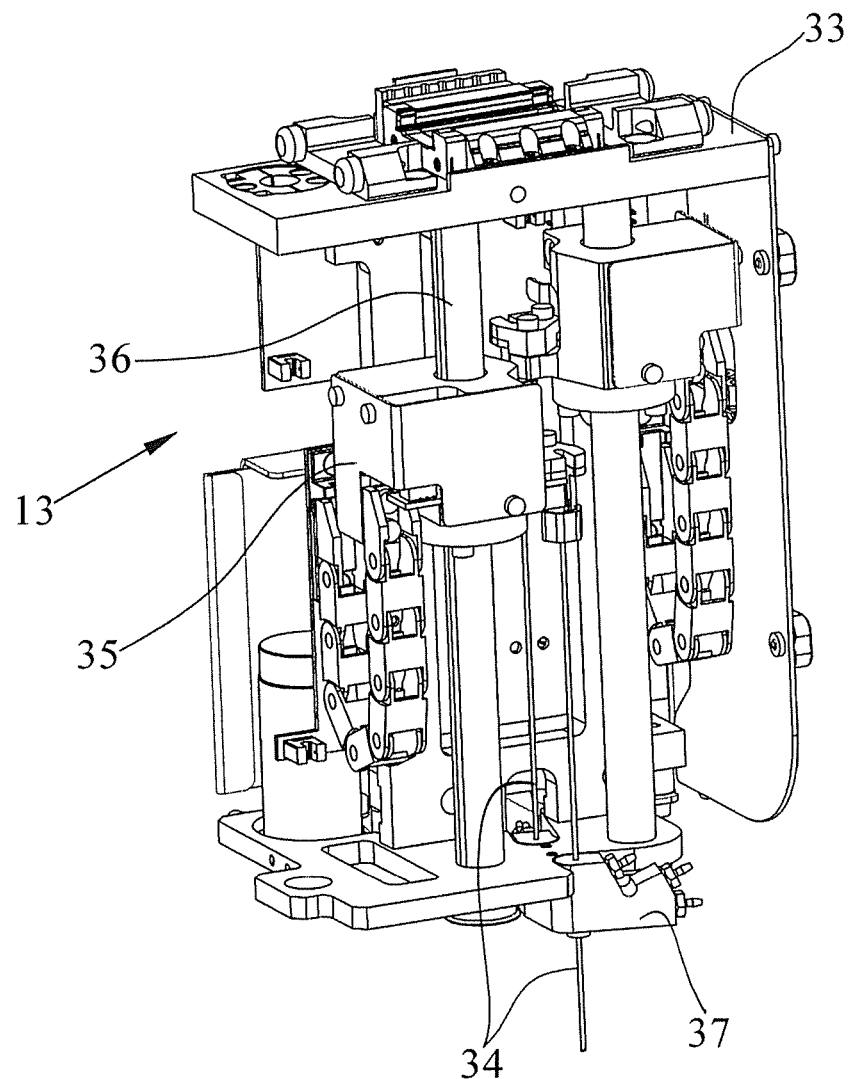
FIG. 11 shows a perspective view of the unit carrying the pipetting probes.
Figure 12:
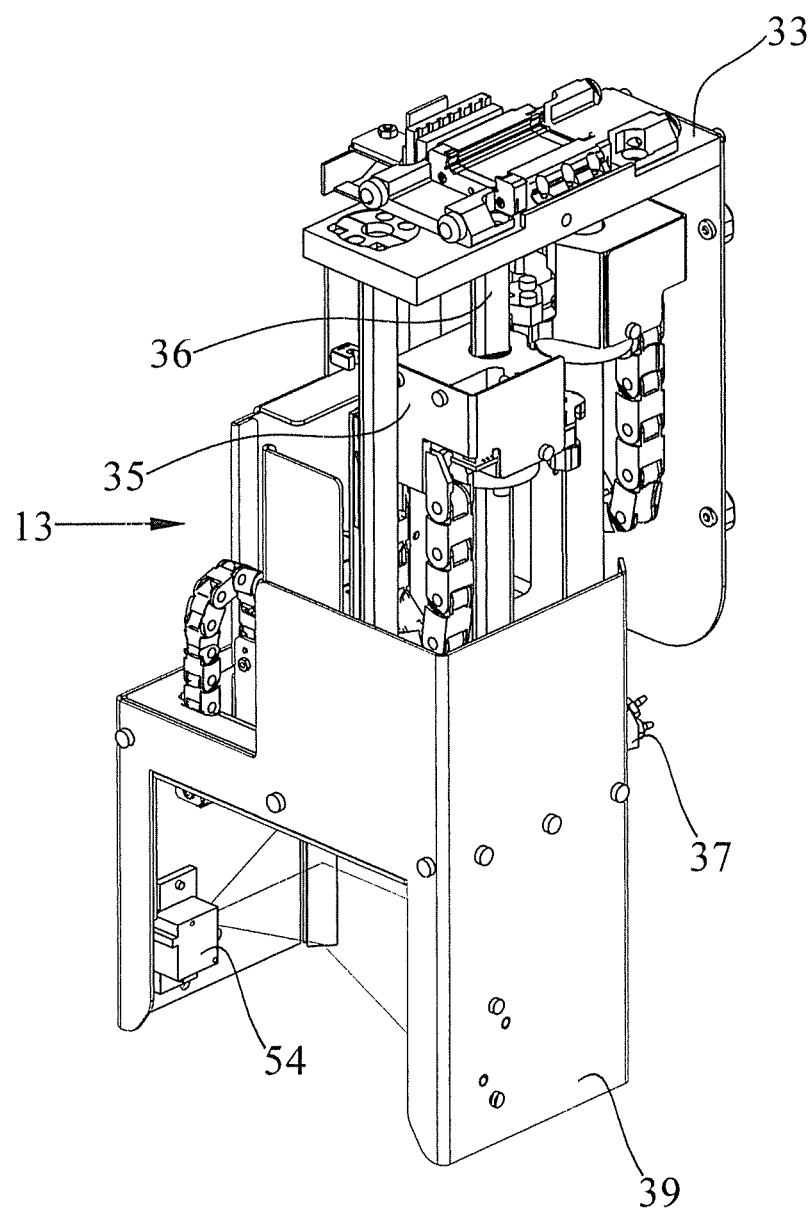
FIG. 12 shows a perspective view similar to that in FIG. 11 incorporating the bar code reader device.

Pipetting unit -13- is shown in greater detail in FIG. 11, its construction being seen by means of an upper card -33- which is the one moving on the guides in the upper part of the upper floor, that is guides -14- illustrated in FIGS. 2 and 3, constructed in such a way that unit -13- can move along the set of coordinate axes X, Y, that is to say covering the entire surface area of the transverse cross-section of the apparatus or, which is the same thing, covering all the surface area of the upper floor shown in FIG. 4 for the purpose of gaining access to any of the cards located in incubators -16- or any of the containers for diluents, reagents or samples in supports -6- and -7-. Unit -13- has two pipetting probes -34- which move vertically independently through the action of unit -35- guided on vertical guide -36-, also having wash pipetting probe -37- which will be explained in greater detail below. Likewise it is provided with two bar code detectors, one of which -54- can be seen in FIG. 20 and a laser detector for the presence of sample tubes and vials/bottles of reagents/diluents in the boxes, which is not shown.

Figure 13:
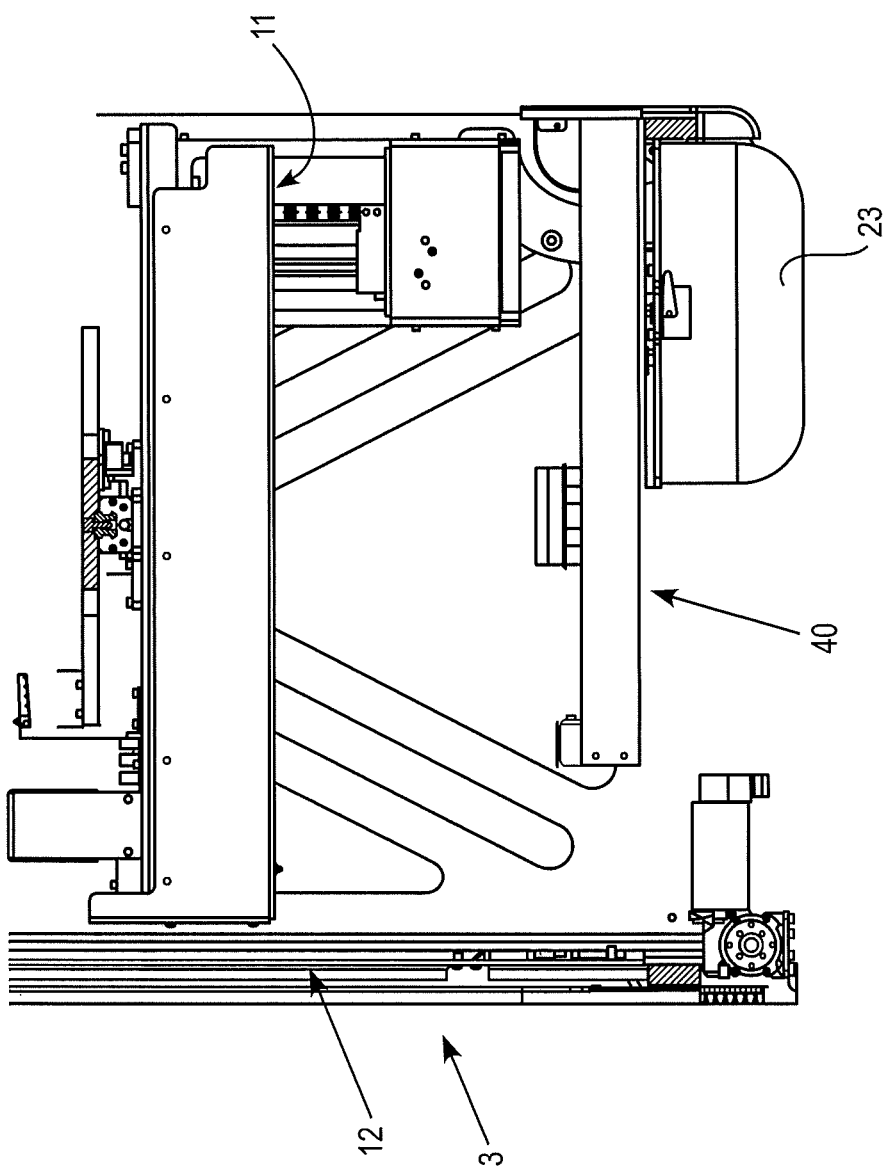
FIG. 13 shows details of a cross-section in which the arrangement of a centrifuge, the card carrying head and intermediate floor can be seen.

FIG. 13 shows a detail of intermediate floor -3- in which will be seen one of centrifuges -23- suspended from floor -40- of the intermediate compartment.

As will be seen, the centrifuges are suspended and can be accessed via the lower floor of the apparatus, it being easy to remove them as they are merely attached to intermediate floor -40-. This appreciably simplifies fitting and servicing of the centrifuges. Access to the cards in them takes place through windows in floor -40- indicated by numbers -41- and -42- and shown in FIG. 5.

Figure 14:
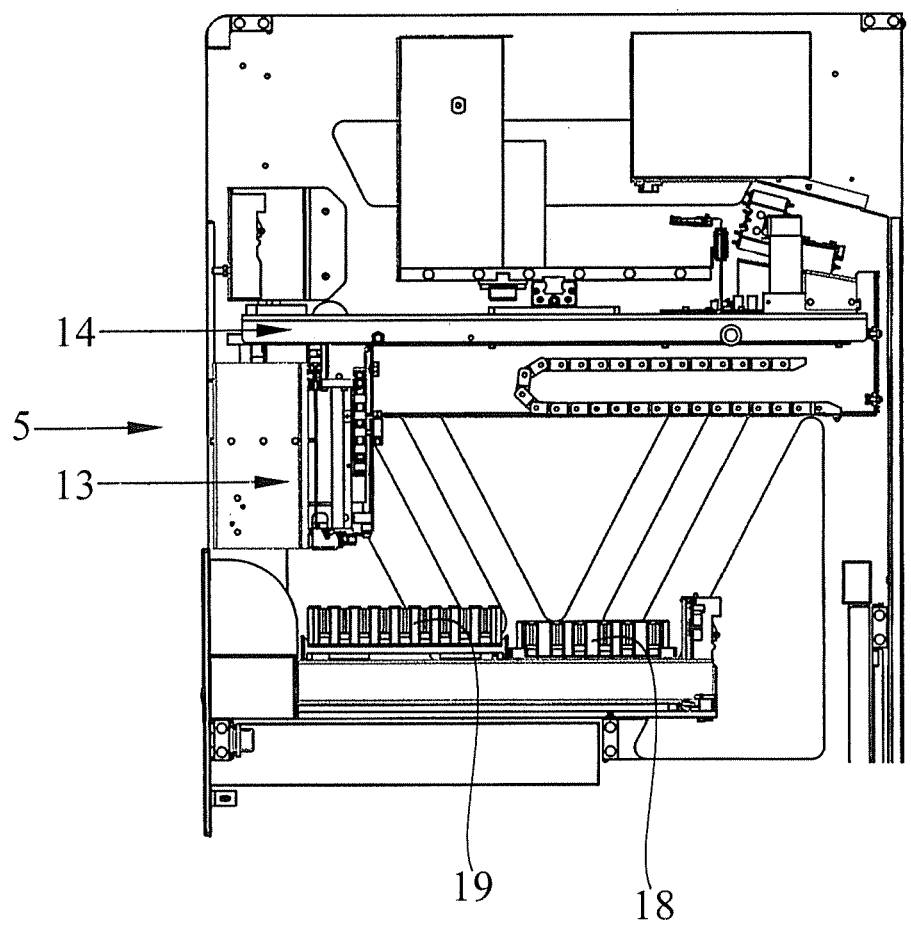
FIG. 14 shows another detail of the upper floor.

FIG. 14 shows a detail of upper floor -5- in which will be seen supports -18- and -19- for containers of diluents and reagents as well as unit -13- which moves along guides -14- moving over the entire surface area of that intermediate floor.

Figure 15:
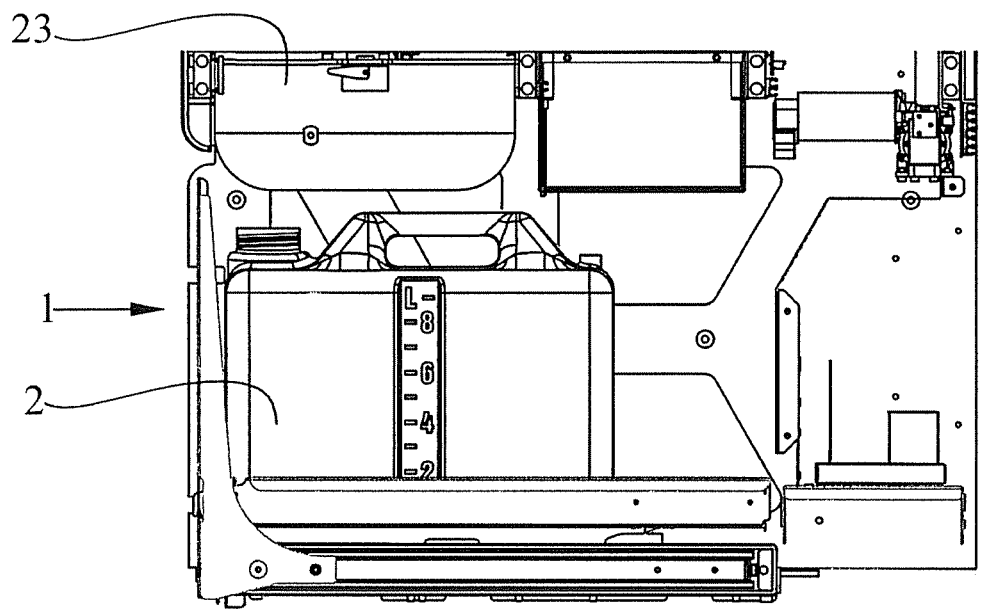
FIG. 15 shows a detail of the lower floor and a centrifuge.

FIG. 15 shows a view similar to that in FIGS. 13 and 14 corresponding to lower floor -1- on which will be seen a centrifuge -23- and one of containers -2- intended to contain wash solutions, waste liquids and others.

Figure 16:
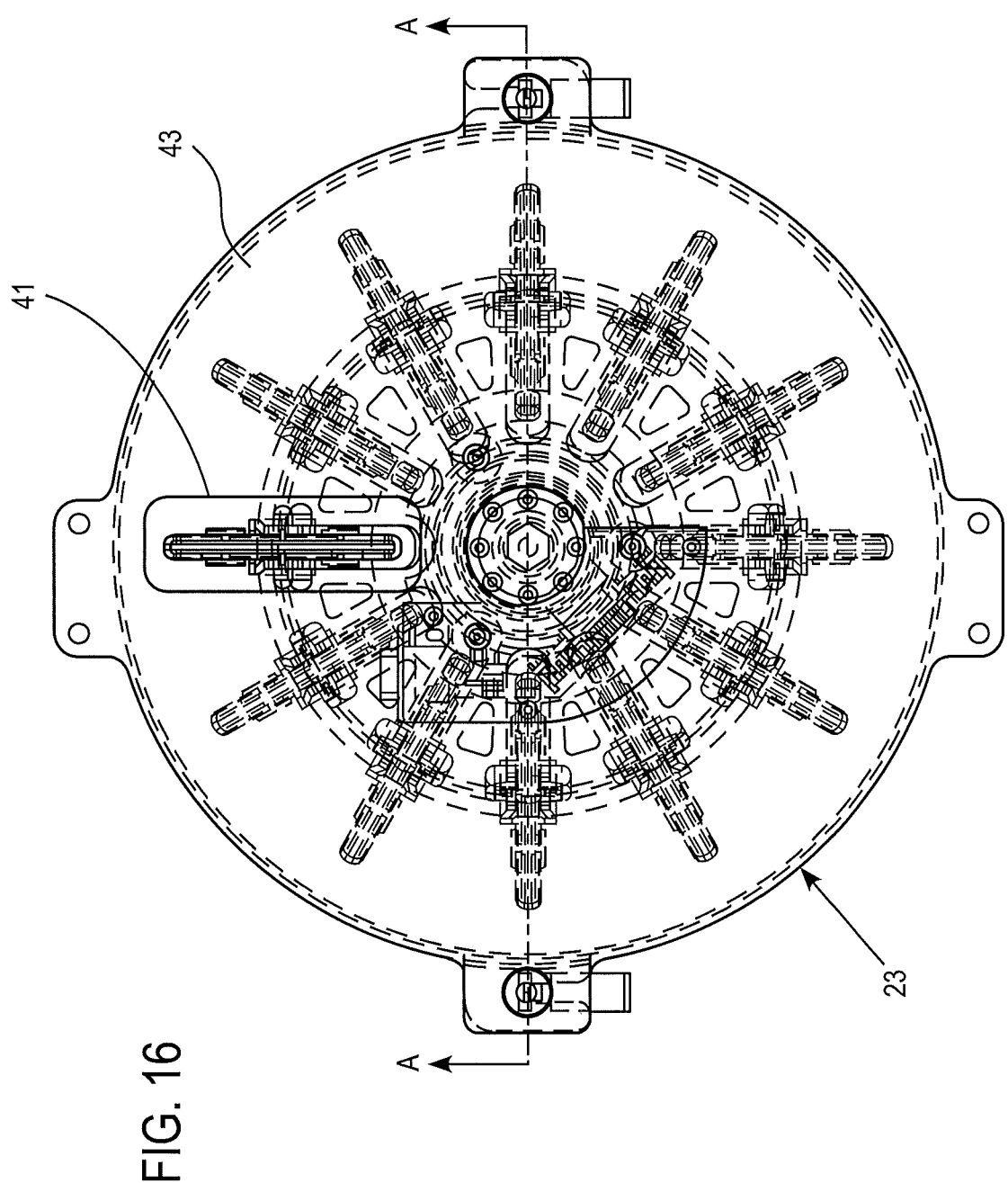
FIG. 16 is a plan view of one of the centrifuges.
Figure 17:
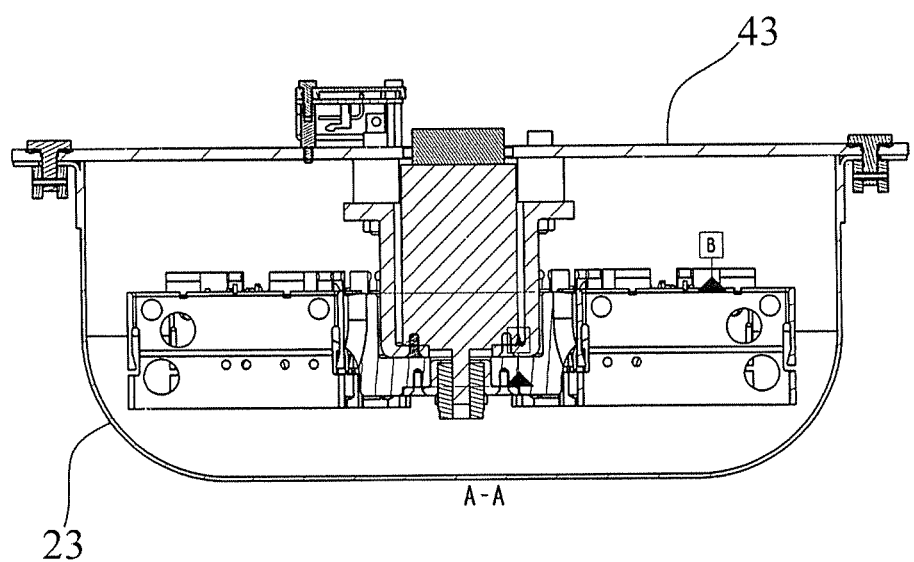
FIG. 17 is a cross-section along the plane A-A in FIG. 16.

FIGS. 16 and 17 show a plan view and a cross-sectional view respectively of a centrifuge, it being seen that centrifuge -23- has an upper cover -43- through which it can be attached, suspending the centrifuge and providing access through an opening -41- which allows the gel card to be positioned and removed through the upper part by means of moving head -10- which carries the carrying clamp for the gel card. The suspended mounting of the centrifuge such that the card supports are located radially with respect to the central axis of rotation will be seen in the cross-section.

Figure 18:
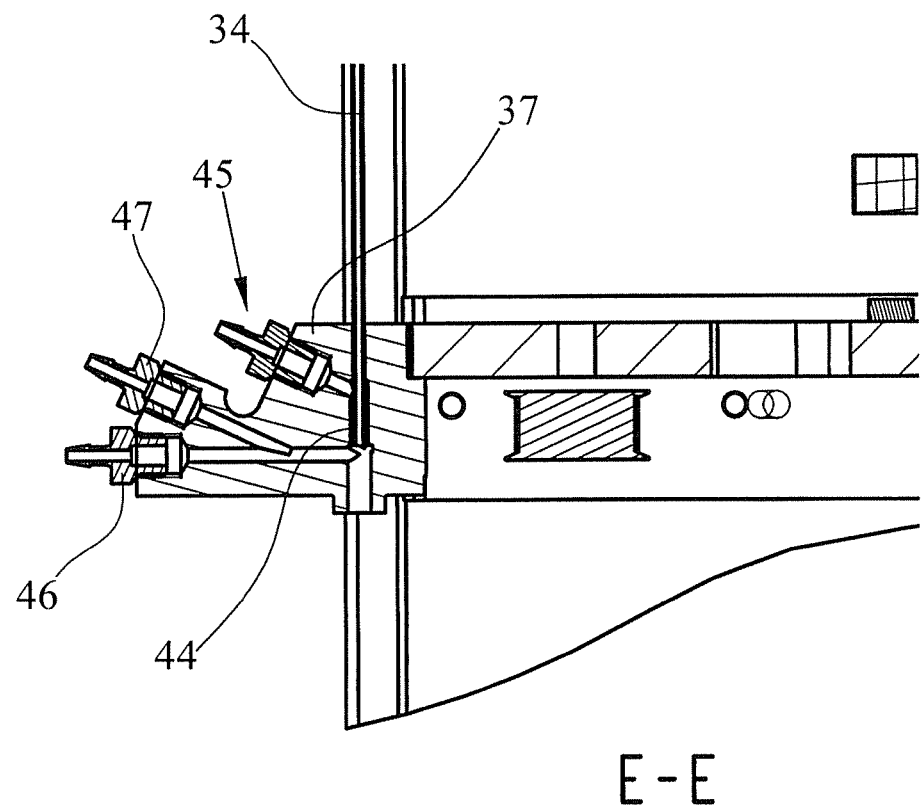
FIG. 18 shows diagrammatically in detail the arrangement for washing the pipetting probes in the external washing position.
Figure 19:
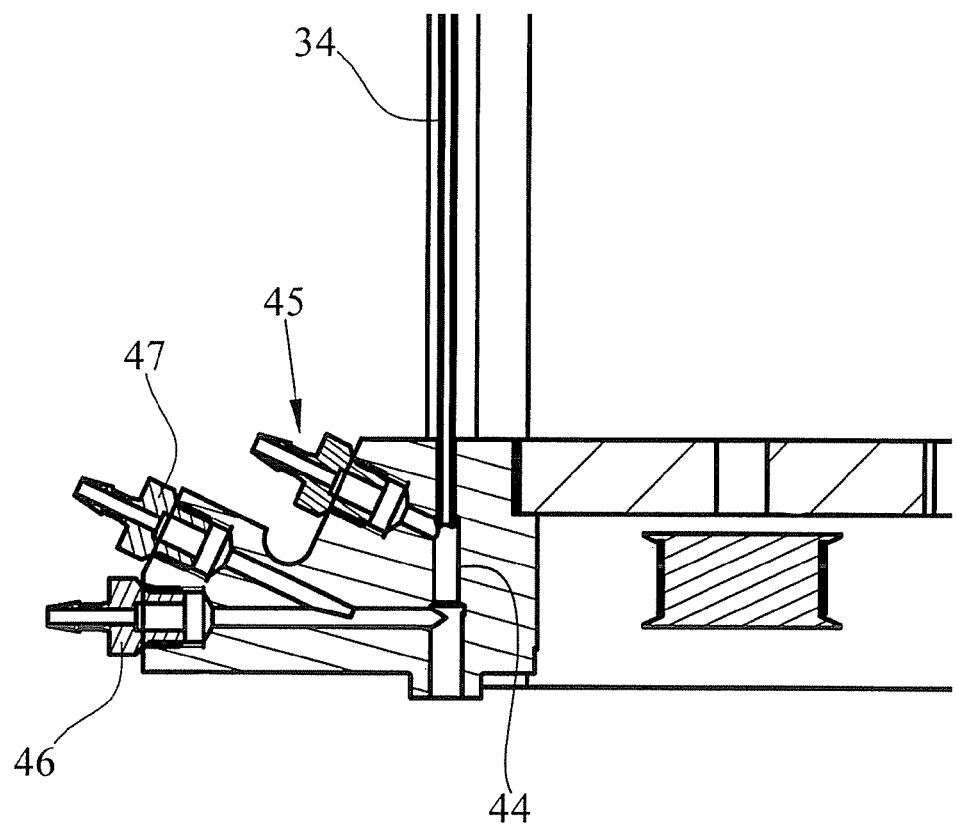
FIG. 19 shows a detail similar to that in FIG. 18 showing internal washing of the pipetting probes.

FIGS. 18 and 19 show details of washing each of the two pipetting probes -34-. The pipetting probes which move along the guide conduit reach the interior of block -37- in which tubular area -44- of somewhat greater diameter receives the wash liquid through one of outlets -46- and -47-, cleaning the outside of the pipetting probe and being sucked up by outlet opening -45-. After the external cleaning cycle the pipetting probe is washed internally in the arrangement shown in FIG. 19 in which pipetting proble -34- has moved upwards releasing tubular part -44- thus allowing the inside to be washed. If necessary the cycle can be repeated.

Figure 20:
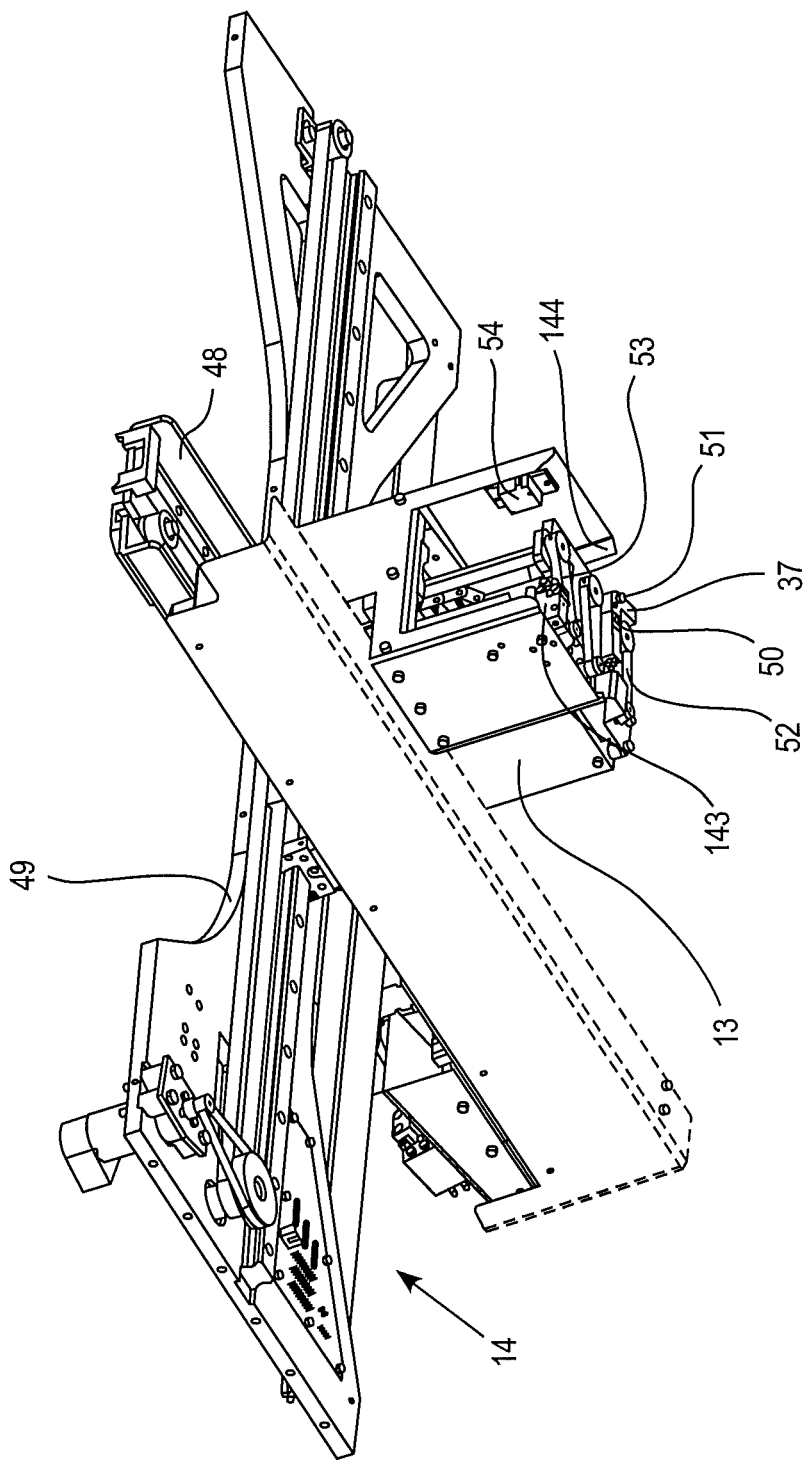
FIG. 20 shows a perspective view of the supporting structure of the unit carrying the pipetting probes, from beneath.

FIG. 20 shows the mounting for the unit carrying the pipetting probes indicated by the number -13-, suspended from a set of guides previously indicated by number -14- in FIG. 2 which essentially comprises one cross-member -48- on which unit -13- moves longitudinally and another cross-member -49- along the guides of which cross-member -48- moves. This brings about movement in two axes at right-angles enabling unit -13- to move to any point on the upper floor for pipetting purposes.

The same figure shows outlets -50- and -51- from the pipetting probes, as well as guiding and washing block -37-, and pipetting probe operating devices -52- and -53-.

Within the reader device enclosure there is also bar code reader -54- and its mirror -144- to aid reading. The laser presence detector -143- will also be seen. Thus the same reading and detector portion includes the bar code reader and the laser presence detector which acts through proximity.

Figure 21:
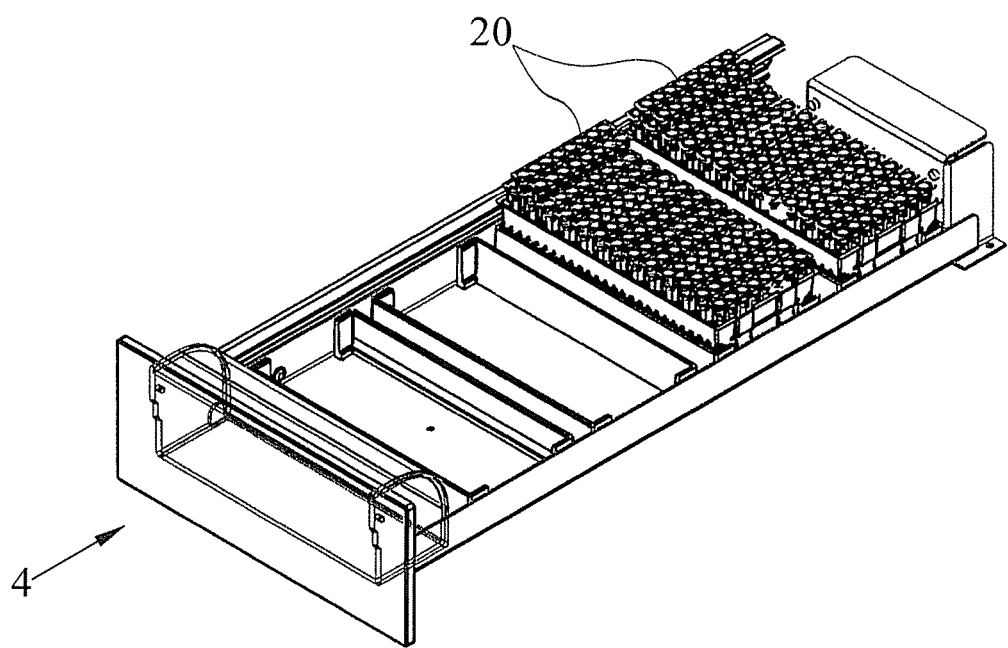
FIG. 21 is a perspective view of a support or box for the "racks" of gel cards.

FIG. 21 shows a perspective view of a support for holding gel cards, this support being identified by numeral -4- as in FIG. 5, showing the arrangement of two of the card supports -20-. Removal of individual cards from the supports -20- takes place by means of unit -10- shown in FIG. 2, which has a clamp for transport and subsequent release of the gel card. These movements take place essentially between supports -20- and the incubators and from there to the upper floor of the apparatus where the pipetting probe can insert the samples for analysis. The entire functioning of the apparatus is automatically controlled by its electronic controller, which is not shown and which is preferably incorporated in the upper part of the apparatus, being accessible via a retractable touch screen -9- which is shown in greater detail in FIGS. 29 and 30. In these it will be seen that the screen comprises a folding assembly formed by a frame -55- and the screen proper -56-, which is folded against it and screen front member -9-. When front member -9- is withdrawn from the inside of the apparatus screen -56- comes out and permits information to be read and instructions to be exchanged with the apparatus. In this respect it must be borne in mind that the characteristics of the apparatus allow it to function completely automatically without impeding access to the cards, reagents, liquids or other components of the apparatus without interrupting its automatic operation.

Figure 22:
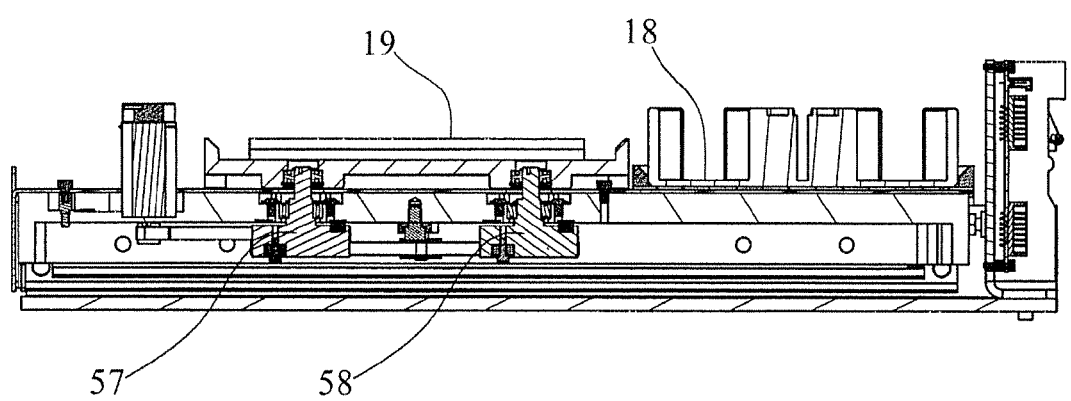
FIG. 22 shows a longitudinal cross-section illustrating some of the elements holding reactants and diluents and orbital stirring means.
Figure 23:
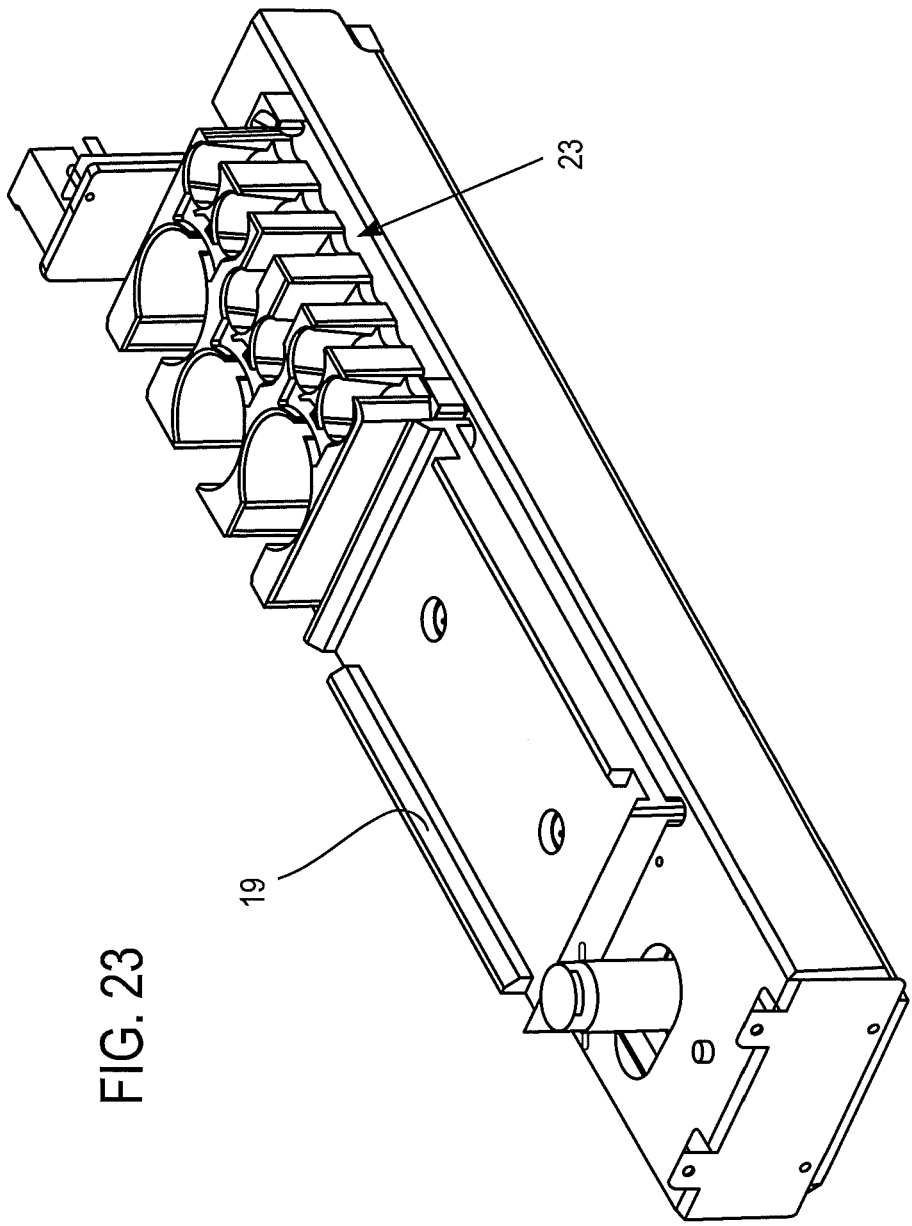
FIG. 23 shows a perspective view of the items illustrated in FIG. 22.

As explained previously in connection with FIG. 4, the supports for samples, reagents and diluents are included on the upper floor and some of these, for example those located on supports -19- can be orbitally stirred so that as shown in FIGS. 22 and 23 support -19- receives the force of two eccentric masses -57- and -58-, FIG. 22, which bring about orbital displacement of support -19- and therefore the containers located above it. The stirring time is controlled by the microcontroller for the apparatus.

Figure 24:
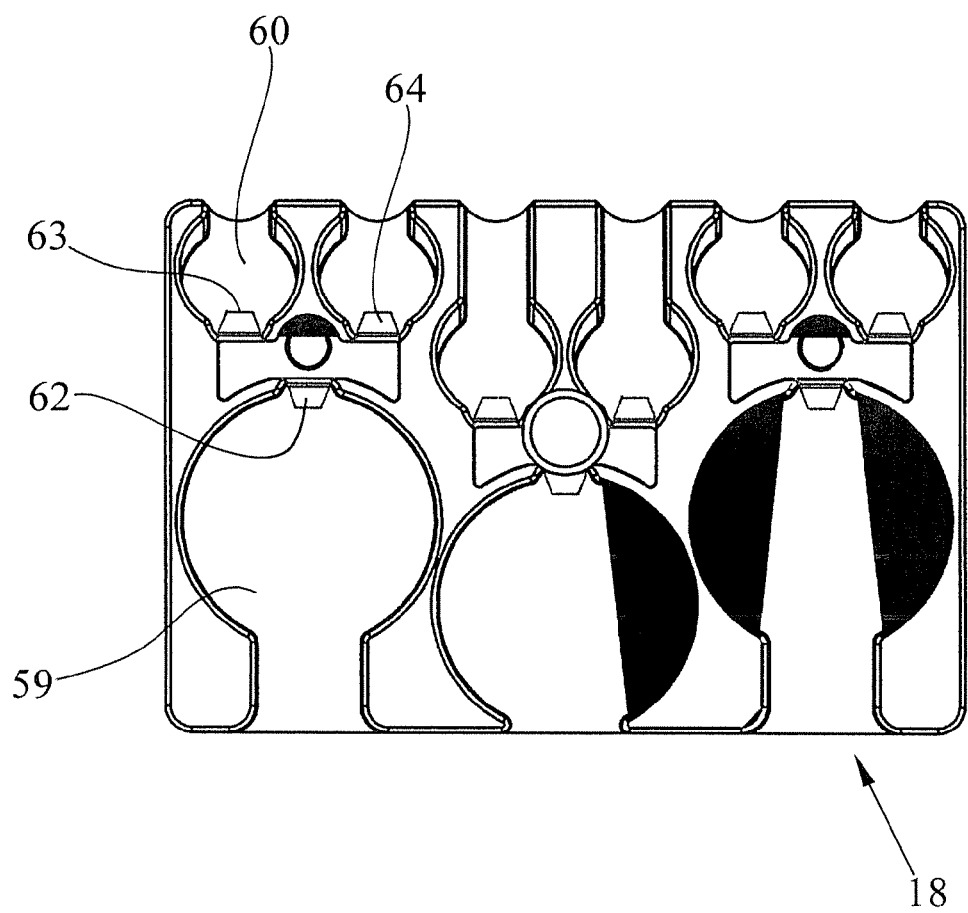
FIG. 24 shows a plan view of a support for reagents.
Figure 25:
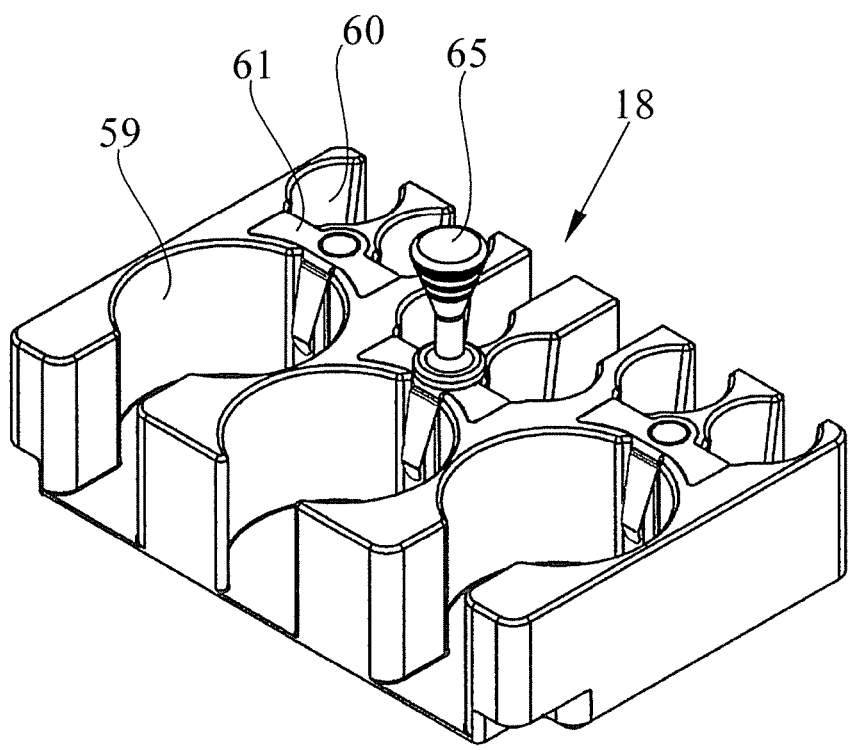
FIG. 25 shows a perspective view of the support for reagents in FIG. 24.

FIGS. 24 and 25 show a view in plan and in perspective respectively of the supports for locating diluents and reagents -18-. The spaces are of adequate size for the containers which they are to contain, in this case cavities of larger diameter -59- and others of smaller diameter -60- grouped in pairs are shown, the arrangement of the laminar springs inserted between the intermediate walls -61- to laterally restrain the containers mounted on supports -18- when these are subjected to the stirring generated by the base of support -19- being shown. These retaining springs are represented by the numbers -62-, -63- and -64- for the set comprising one cavity -59- and two cavities -60-. Preferably these retaining elements are associated with an upper handling handle -65-.

Figure 26:
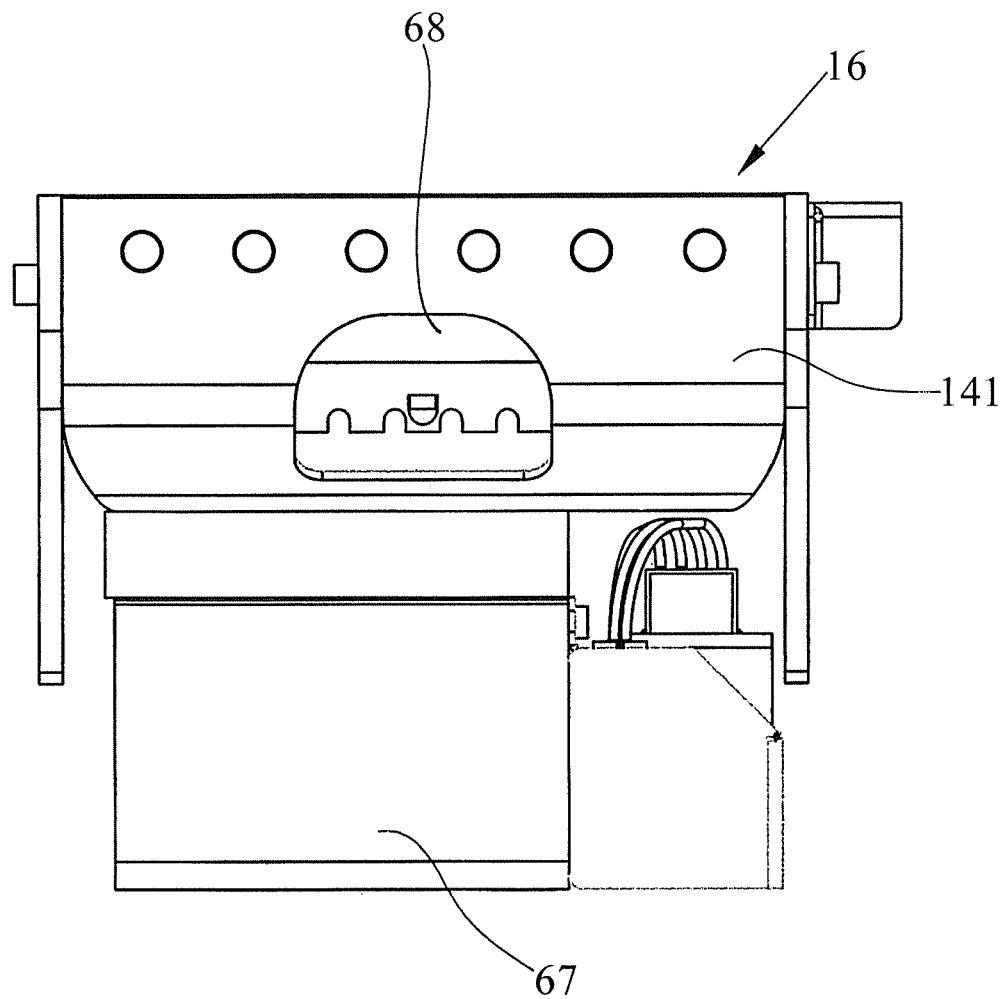
FIG. 26 shows a diagrammatical side view of a heating device.
Figure 27:
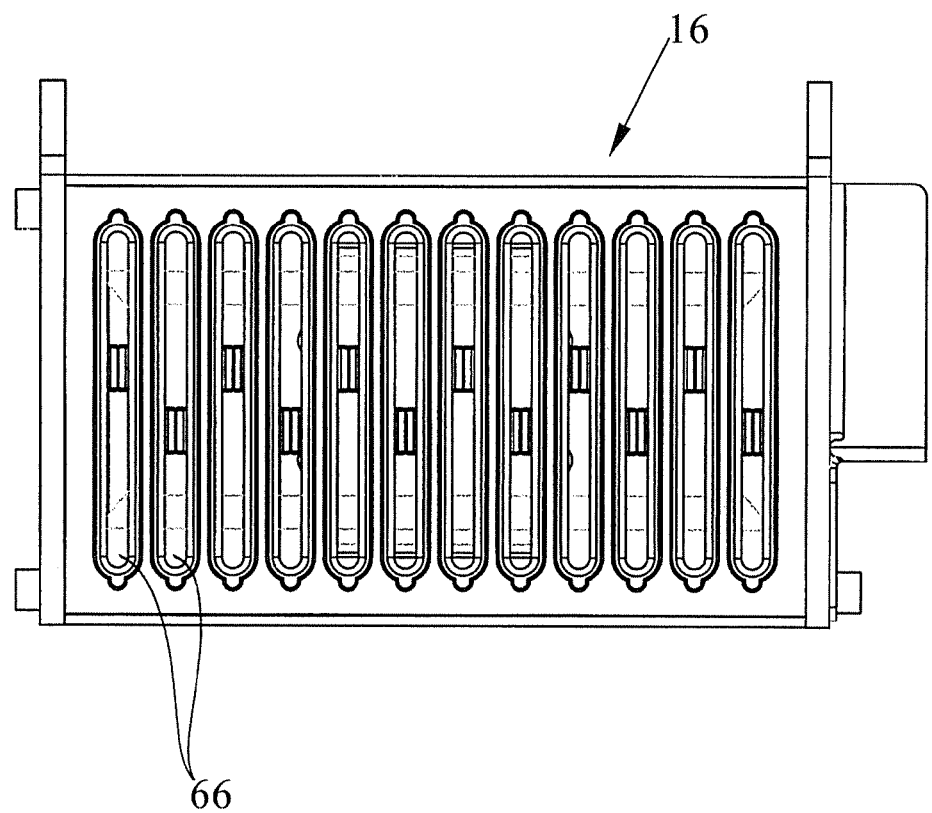
FIG. 27 shows a plan view of a gel card heating device.

FIGS. 26 and 27 show an incubator device -16-, of aluminium for the better transmission of heat, intended to contain multiple cards in cavities -66-, also having means for heating the same incorporated in a Peltier unit -67- physically attached to the incubator or card support -16- through a wide U-shaped piece -141- provided laterally with windows -68- intended to allow the same heat flow to the various cavities -66-, compensating for the difference in heat flow between heater device -67- and said cavities -66-.

Figure 28:
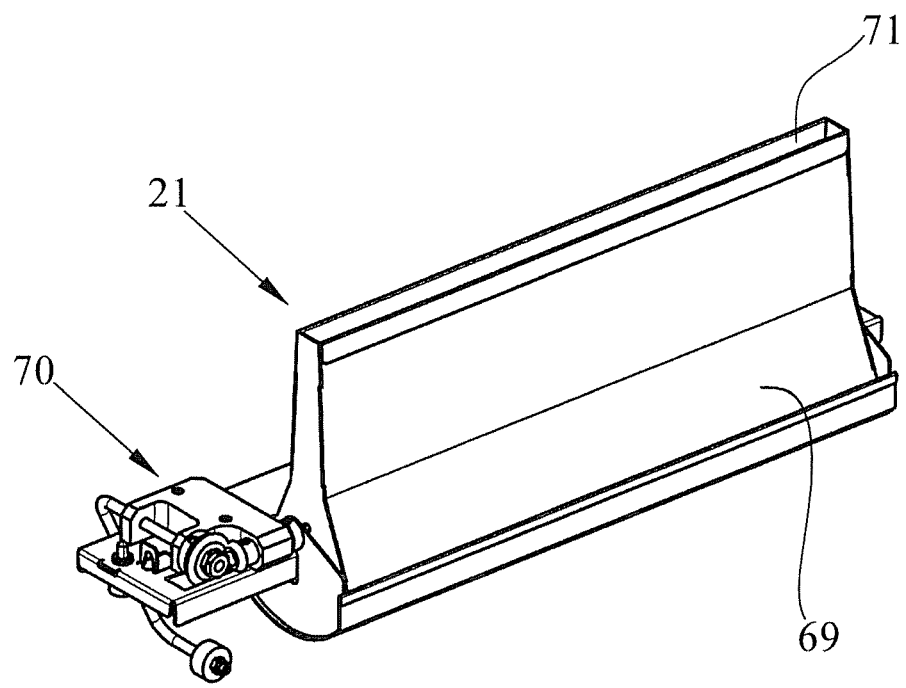
FIG. 28 shows a perspective view of a buffer device for collecting waste on the lower floor.

FIG. 28 shows a perspective view of a buffer collector -28- for waste cards after the process of analysis in the apparatus when the main box has been removed for emptying. This collector -21- has a bag-shaped body -69- at the bottom and rotates around a longitudinal geometrical axis through a device -70- which has in its top a longitudinal groove -71- in which the card transporter deposits those which have to be discarded when the main box is not in position. The apparatus has a tilting door activated by the main waste box when the box is opened. The door then closes and the assembly behaves as a box. When the main waste box is inserted into the apparatus it operates a lever and opens the tilting door, the cards falling into the main box.

FIGS. 31 and 32 show in greater detail the retractable platform or worktop -9- illustrated in FIG. 1. This worktop has a front -8- and a top surface -72- associated with supporting frame -74-. In this way the operator can easily have a platform or worktop for notes and other minor purposes.

FIG. 33 shows diagrammatically the arrangement of some elements of the fluidic system in the apparatus, intended to feed fluids from a container at constant pressure. The diagram in FIG. 33 shows the general arrangement of a container -75- for the liquid which has to be dispensed, pump -76- connected to proportional valve -77- through tubes -78- and -79-, feeding a liquid at a constant pressure to common distribution point -80- to the various outlet circuits -81- through the corresponding electrically-operated valves -82-. A sensor -83- captures the value of the pressure at common point -80- and transmits it to electronic control units -84- which in turn controls proportional valve -77-.

FIGS. 34 and 35 each show diagrams of the process according to the invention in which the various stages of operation will be seen. FIG. 34 shows the process in general from filling the apparatus to review and display of the results and FIG. 35 shows diagrammatically the management of the contents which may occur at any time during the process.

One of the most important features of the process and apparatus to which the invention relates arises from the possibility of combining automatic operation of the apparatus with manual interventions and operation of the apparatus to perform different processes simultaneously with the necessary staggering of operations which might coincide.

FIG. 34 shows loading or unloading -85- of the apparatus which may comprise the loading/unloading of samples -86-, after which the subsequent stage -87- of sample location and identification is performed and after this the working load -88- is assigned, either automatically -89- or manually -90-. After this preparation for initiating the working load -91- takes place, in which successive processes indicated by readers -92- are initiated while there are resources and pending work, and performed in parallel with successive offsets. Preparation to begin the working load comprises various operations such as the stirring of reagents -93-, checking the integrity of microtubes -94- using the multiple reader device, preparing incubators -95- and filling incubators -96-. After this the incubator in which the processing stage -96- is to be performed is raised, with subsequent pipetting -97- according to the sequence and parameters defined previously, with the possibility for dispensing serum -97-, dilution and homogenisation of the sample -98-, especially red blood cells, the dispensing of reactive red blood cells -99-, the dispensing of other reagents -100- and washing of the pipetting probes and dilution well -101-. Then in stage -102- the incubator is lowered to the intermediate floor in the apparatus, incubation taking place in stage -103- according to different controlled parameters -104-, such as time -105- and temperature -106-. The cards are then transported from the incubator to the centrifuge in stage -107-, followed by centrifuging -108-. During this various parameters -109-, especially speed -110-, time -111-, acceleration -112- and braking -113- will be taken into account. Then a card is transported from the centrifuge to the reading head during the stage indicated by the number -114-, reading -115- being performed with the subsequent sub-stages of recognising clotting in the well in card -116-, checking that the microtubes are intact -117-, checking the dispensed volume -118-, checking responses in the sample, for example, for example lipaemia, haemolysis, etc., and interpreting the result -120-. The card then returns to stage -121- for disposal -122- or may be returned to the operator for manual checking in sub-stage -123-. Finally review and publication of the results takes place in stage -124-, review -125- and printing-out -126- being related to the sub-stages of acceptance -127-, disposal -128-, amendment -129- and repetition -130- respectively, manual intervention being represented by -131- and printing out by the printer by -132-.

FIG. 35 shows the handling of containers -133- which can take place at any time during the process and which may include a number of sub-stages such as the loading and unloading of reagents -134- including the location and identification of reagents such as type, lot and expiry date in sub-stage -135-, loading and unloading of cards in sub-stage -136- which includes the location and identification of cards, type and expiry date -137-, filling with wash solutions -138-, discharging waste liquids -139- and discharging waste cards -140-.

FIG. 36 shows the rack -150- for reagents, with quincunx arranged cavities -151- and -152-.

FIGS. 37 and 38 show perspective views of card carrier unit -10-, with clamp -153- and laser presence detectors -154- and bar code reader -155-.

As will be understood, the description and accompanying drawings are in the nature of a non-restrictive example, as a result of which the modifications and changes which may be introduced by those skilled in the art after reading and understanding this patent application are included within the scope of the invention and fall within the scope of the following claims and their equivalents.

The invention claimed is:

1. An apparatus for the automatic analysis of samples on gel cards, comprising compartments superimposed in a single cabinet, each compartment having a floor, a heating and lifting assembly comprising a heater electrically connected by a flexible connection and configured to displace said gel cards between at least two of the compartments, and having in at least one of the compartments a card transport unit configured to displace said gel cards along the entire transverse cross-section wherein movement of said gel cards is effected by a control computer.

2. An apparatus for the automatic analysis of samples on gel cards according to claim 1, further comprising a removable box with one or more containers for wash liquids, waste liquids and waste cards in the lower compartment.

3. An apparatus for the automatic analysis of samples on gel cards according to claim 2, wherein the box for waste cards further comprises an auxiliary buffer container for waste cards having a bag-shaped body and a tilting door configured to close when the box for waste cards has been removed.

4. An apparatus for the automatic analysis of samples on gel cards according to claim 1, further comprising an electronic control means for the successive and staggered coordination of the stages of different processes of analysis to permit continuous operation of the apparatus without interruption.

5. An apparatus for the automatic analysis of samples on gel cards according to claim 1, wherein said heating and lifting assembly further comprises vertical guides, and supports for gel cards that can be moved on said guides, and wherein said guides are configured to transport said gel cards between the different floors.

6. An apparatus for the automatic analysis of samples on gel cards according to claim 5, wherein said heating and lifting assembly comprises a lower heating unit associated with the supporting body which has multiple locations for the gel cards and clamps to prevent the gel cards being moved during pipetting.

7. An apparatus for the automatic analysis of samples on gel cards according to claim 6, wherein the clamps for retaining the gel cards in the incubator housings comprise movable cards located opposite each other and provided with magnetic means which attract each other, clamping the cards located between pairs of these cards.

8. An apparatus for the automatic analysis of samples on gel cards according to claim 6, wherein the body holding the housings for the gel cards associated with the heat generating unit is made of a material having a high thermal transmission coefficient and is provided with lateral windows to render the heat path between the heat generating unit and the various housings for the gel cards uniform so that they are heated evenly.

9. An apparatus for the automatic analysis of samples on gel cards according to claim 1, further comprising an intermediate compartment containing multiple boxes removable from the front, which allow the original card supports to be inserted, any of the cards being accessible by means of a unit carrying a transporting clamp for the same which can be moved along coordinates X, Y, Z at right-angles covering the entire transverse surface area of the apparatus, providing access to both the gel cards and the incubation supports for the same, the lower position of which along their vertical movement guides substantially coincides with the level of the gel cards located in the boxes, the unit being further equipped with a bar code reader for the labels on the cards and a laser sensor to detect whether cards are present in the supports of the boxes.

10. An apparatus for the automatic analysis of samples on gel cards according to claim 9, wherein the intermediate compartment has a body in a fixed arrangement with a reading device for the gel cards for interpreting the results, which is accessible by means of the unit carrying the transport clamp for the gel cards.

11. An apparatus for the automatic analysis of samples on gel cards according to claim 9, wherein the removable boxes carrying the original supports for the gel cards are located with separations between the said boxes to permit the gel cards to pass vertically to and from the centrifuges and/or other devices such as the reader or to the card disposal box.

12. An apparatus for the automatic analysis of samples on gel cards according to claim 1, wherein the centrifuges for the cards hang beneath the boxes in the supporting structure within the apparatus assisting their fitting and removal through the bottom thereof for the purposes of maintenance, cleaning and other purposes.

13. An apparatus for the automatic analysis of samples on gel cards according to claim 12, wherein the centrifuges are fitted with upper covers with an opening for the entry and removal of one of the gel cards by means of the carrier unit of the clamp carrying the cards.

14. An apparatus for the automatic analysis of samples on gel cards according to claim 1, wherein the upper compartment of the apparatus has boxes which can be removed from the front for the insertion of reagents, boxes which can be removed from the front for the insertion of samples and a double container for diluting samples, in addition to a unit which can be moved along coordinate axes X, Y, Z at right-angles in such a way that it covers the entire transverse surface area of the apparatus to gain access to all the elements located in the upper compartment and also the incubators in the high position at the level of the reagent and sample containers.

15. An apparatus for the automatic analysis of samples on gel cards according to claim 14, wherein the unit which can be moved along coordinate axes at right-angles in the upper compartment has removable and independently controllable pipetting probes for pipetting operations into two card wells, into reagent containers, into sample containers or into the device or double well for performing dilutions.

16. An apparatus for the automatic analysis of samples on gel cards according to claim 15, wherein the said unit includes a laser presence detector to detect the presence of containers of reagents and samples and to determine the diameter of the sample tubes, as well as bar code readers associated with a body which can move vertically with respect to the said unit so that the readers can be located on both sides of each reagent or sample box thus permitting the codes on the labels of the said reagents and the said samples to be read.

17. An apparatus for the automatic analysis of samples on gel cards according to claim 15, wherein the movable unit carrying the pipetting probes is associated with a block for washing the same comprising tubular conduits surrounding the pipetting probes each of which are fed independently with wash and rinsing liquids from the lower floor, and having conduits located in a higher position than the inlet conduits for collecting the used wash liquids for the purpose of leading them to the discharge.

18. An apparatus for the automatic analysis of samples on gel cards according to claim 14, further comprising a block in the upper compartment which includes all the electronic control elements, including the source of power and the control computer.

19. An apparatus for the automatic analysis of samples on gel cards according to claim 14, wherein the double container for performing sample dilutions comprises a fixed support carrying an upper body with a double cavity for dilutions, each of the said cavities having their own inlet and outlet openings for the liquids and the said body being attached to the fixed support by means of a resilient block and having beneath a rotatable eccentric mass which is capable of imparting an orbital stirring movement to the upper body supporting the dilution cavities.

20. An apparatus for the automatic analysis of samples on gel cards according to claim 1, further comprising a unit for controlling the feed and pressure of the liquids used in the apparatus which comprises a feed conduit to a point where conduits branch off to the various electromagnetic valves, with an impeller pump located in the said conduit, and as a branch with respect to each pump a proportional valve powered through an electronic control connected to a sensor for the pressure of the liquid at the feed point to the electromagnetic valves, so that the feed pressure to them can be controlled.

* * * * *